(12) United States Patent
Deppermann et al.

(10) Patent No.: US 9,598,191 B2
(45) Date of Patent: Mar. 21, 2017

(54) HIGH SPEED COUNTER

(71) Applicant: Monsanto Technology LLC, St. Louis, MO (US)

(72) Inventors: Kevin Deppermann, St. Charles, MO (US); Elias J. Yannakakis, Chesterfield, MO (US); Allen N. Ondes, Golden Eagle, IL (US); Brian J. Forinash, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 14/554,417

(22) Filed: Nov. 26, 2014

(65) Prior Publication Data
US 2015/0075946 A1 Mar. 19, 2015

Related U.S. Application Data

(63) Continuation of application No. 13/000,961, filed as application No. PCT/US2009/048992 on Jun. 29, 2009, now Pat. No. 8,925,762.
(Continued)

(51) Int. Cl.
| | |
|---|---|
| *B65B 35/30* | (2006.01) |
| *B65B 35/28* | (2006.01) |
| *B65B 57/20* | (2006.01) |
| *A01C 7/04* | (2006.01) |
| *B65G 37/00* | (2006.01) |
| *B65G 47/08* | (2006.01) |

(Continued)

(52) U.S. Cl.
CPC .............. *B65B 35/30* (2013.01); *A01C 7/046* (2013.01); *B65B 35/28* (2013.01); *B65B 57/20* (2013.01); *B65G 37/00* (2013.01); *B65G 47/08* (2013.01); *B65G 47/46* (2013.01); *G05B 15/02* (2013.01)

(58) Field of Classification Search
CPC ............. G07F 17/0092; G06F 19/3456; G06F 19/3462
See application file for complete search history.

(56) References Cited

U.S. PATENT DOCUMENTS

| 3,770,164 A | 11/1973 | Hembree |
| 4,019,651 A | 4/1977 | Starr et al. |
(Continued)

FOREIGN PATENT DOCUMENTS

| WO | 2005090167 A2 | 9/2005 |
| WO | 2005104046 A1 | 11/2005 |

*Primary Examiner* — Timothy Waggoner
(74) *Attorney, Agent, or Firm* — Polster Lieder

(57) ABSTRACT

The present disclosure provides systems and methods for counting a plurality of objects and parsing the objects into groups of varying quantities. In various embodiments, the system includes a singulating and counting module operable to singulate and count a plurality of objects from a large volume of the objects. Additionally, the system includes a diverter and accumulator module operable to receive the singulated objects, parse the objects into groups of varying quantities, and direct each group into a selected one of a plurality of discharge funnels. Furthermore, the system includes an object collection module operable to sequentially position each one of a plurality of object collection receptacles adjacent the discharge funnels such that each group of objects is deposited into a respective corresponding one of the object collection receptacles.

1 Claim, 21 Drawing Sheets

Related U.S. Application Data

(60) Provisional application No. 61/077,766, filed on Jul. 2, 2008.

(51) Int. Cl.
  *B65G 47/46* (2006.01)
  *G05B 15/02* (2006.01)

(56) References Cited

U.S. PATENT DOCUMENTS

| | | |
|---|---|---|
| 4,383,540 A | 5/1983 | De Meyer et al. |
| 5,170,909 A | 12/1992 | Lundie et al. |
| 5,348,061 A * | 9/1994 | Riley ................ G07F 17/0092 |
| | | 141/104 |
| 6,561,377 B1 | 5/2003 | Pearson et al. |
| 6,799,413 B2 * | 10/2004 | Aylward .................. B65B 1/14 |
| | | 53/501 |
| 6,799,684 B2 | 10/2004 | Wooldridge |
| 6,899,144 B1 * | 5/2005 | Geltser ..................... A61J 7/02 |
| | | 53/501 |
| 6,932,236 B2 | 8/2005 | Ven Huizen |
| 7,412,302 B2 * | 8/2008 | Cobb ................. G07F 17/0092 |
| | | 700/243 |
| RE42,730 E * | 9/2011 | Lasher ......................... 53/131.4 |
| 8,091,733 B2 * | 1/2012 | Janet .......................... A61J 7/02 |
| | | 211/9 |
| 2005/0224510 A1 | 10/2005 | Remis et al. |
| 2006/0025884 A1 * | 2/2006 | Henkel .................. B65B 5/103 |
| | | 700/216 |

\* cited by examiner

HIGH SPEED COUNTER

RELATED APPLICATIONS

This application is a Continuation of U.S. patent application Ser. No. 13/000,961, filed on Feb. 18, 2011, which is a National Stage of International Application No. PCT/US2009/048992, filed Jun. 29, 2009, which claims priority to U.S. Provisional App. No. 61/077,766, filed on Jul. 2, 2008. The disclosures of which are incorporated herein by reference in their entirety.

TECHNICAL FIELD

The present disclosure relates generally to systems and methods for counting small objects, such as seeds, at a high rate of speed and accuracy.

BACKGROUND

The statements in this section merely provide background information related to the present disclosure and may not constitute prior art.

In various operations, it is necessary to repetitively separate selected numbers of small objects from bulk quantities of the respective small objects. For example, in object analytics, breeding, planting, storage, packaging etc. operations it is often necessary to separate a plurality of various quantities of objects from a much larger bulk amount of objects. To separate the selected, or desired, number of small objects from the bulk amount, counting devices are often employed. At least some known counting devices measure the mass and/or weight of the objects to approximately determine the number or amount of objects that have been parsed from a larger quantity of the objects.

Alternatively, at least some other known counting devices comprise a vibratory bowl feeder that is constructed to receive a bulk amount of small objects and operational to feed the objects down a track where each object passes a photoelectric eye to be counted. The counted objects are then funneled into a chute or tube having a collection receptacle, e.g. a container, beaker, cup, envelope, bag, etc. removably attached to or positioned under an end of the chute or tube for receiving the counted small objects. Once a desired number of small objects have been counted and deposited into a collection receptacle, the counting device must be stopped so that the collections receptacle can be removed and replaced with a subsequent receptacle by operations personnel. Thus, operations personnel must manually interact with the counting device after each individual desired amount of small objects is parsed, counted and deposited into a respective collection receptacle.

SUMMARY

The present disclosure provides systems and methods of individually separating small objects from a large volume of objects, i.e., singulating the objects, counting the singulated objects, parsing the singulated objects into groups of varying quantities, and depositing each parsed group of objects into a corresponding collection receptacle at a high rate of accuracy and speed. The methods are particularly adapted for automation, which provides greater sorting efficiency and throughput rate than was previously practical.

In various other embodiments, the system includes a singulating and counting module that is structured and operable to singulate a plurality of objects from a large volume of the objects and count the singulated objects. Additionally, the system includes a diverter and accumulator module that is structured and operable to sequentially receive the singulated objects, sequentially separate, or parse, the received objects into groups of objects of varying quantities. That is, each group of objects comprises an automatically controlled number of objects wherein at least one of the groups of objects comprises a different number of objects than at least one other group of objects. The diverter and accumulator module is additionally structured and operable to direct each group of singulated objects into a selected one of a plurality of discharge funnels of the diverter and accumulator module. Furthermore, the system includes an object collection module that is structured and operable to automatically sequentially position each one of a plurality of object collection receptacles adjacent to the discharge funnels such that each group of objects is deposited into a respective corresponding one of the object collection receptacles.

In various other embodiments, the method includes singulating a plurality of objects from a large volume of the objects and counting the singulated objects, wherein the singulating and counting is performed utilizing a singulating and counting module. The method additionally includes sequentially receiving the singulated objects and sequentially separating the received objects into groups of objects such that each group of objects comprises an automatically controlled number of objects and at least one of the groups of objects comprises a different number of objects than at least one other group of objects. The method further includes directing each group of singulated objects into a selected one of a plurality of discharge funnels of a diverter and accumulator module, wherein the sequentially receiving, separating and directing is performed utilizing an automatically controlled diverter head of the diverter and accumulator module. Still further, the method includes automatically sequentially positioning each one of a plurality of object collection receptacles adjacent the discharge funnels such that each group of objects is deposited into a respective corresponding one of the object collection receptacles, wherein the automatically sequentially positioning is performed utilizing an object collection module.

In various other embodiments the system includes a singulating and counting module that is structured and operable to singulate a plurality of objects from a large volume of the objects and count the singulated objects. The system additionally includes a diverter and accumulator module that is structured and operable to sequentially receive the singulated objects and sequentially separate the received objects into groups of objects such that each group of objects comprises an automatically controlled number of objects and at least one of the groups of objects comprises a different number of objects than at least one other group of objects. Additionally, the diverter and accumulator module is structured and operable to direct each group of singulated objects into a selected one of a plurality of discharge funnels of the diverter and accumulator module. The system further includes an object collection module that is structured and operable to automatically sequentially position each of a plurality of object collection receptacles adjacent to the discharge funnels such that each group of objects is deposited into a respective corresponding one of the object collection receptacles. Each collection receptacle includes an information device including information indicative of the number of objects to be included in each group of objects to be deposited into each respective collection receptacle, wherein at least one of the groups of objects having a different number of objects than at least one other group of objects. The system still further includes a control system that operable to read each information device, store the read information in an electronic spreadsheet and control and coordinate the operations of the singulating and counting module, the diverter and accumulator module and the object collection module to deposit each group of objects into the respective corresponding collection receptacle based on the information stored in the electronic spreadsheet.

Further areas of applicability of the present teachings will become apparent from the description provided herein. It should be understood that the description and specific examples are intended for purposes of illustration only and are not intended to limit the scope of the present teachings.

BRIEF DESCRIPTIONS OF DRAWINGS

The drawings described herein are for illustration purposes only and are not intended to limit the scope of the present teachings in any way.

DESCRIPTION

Figure 1:
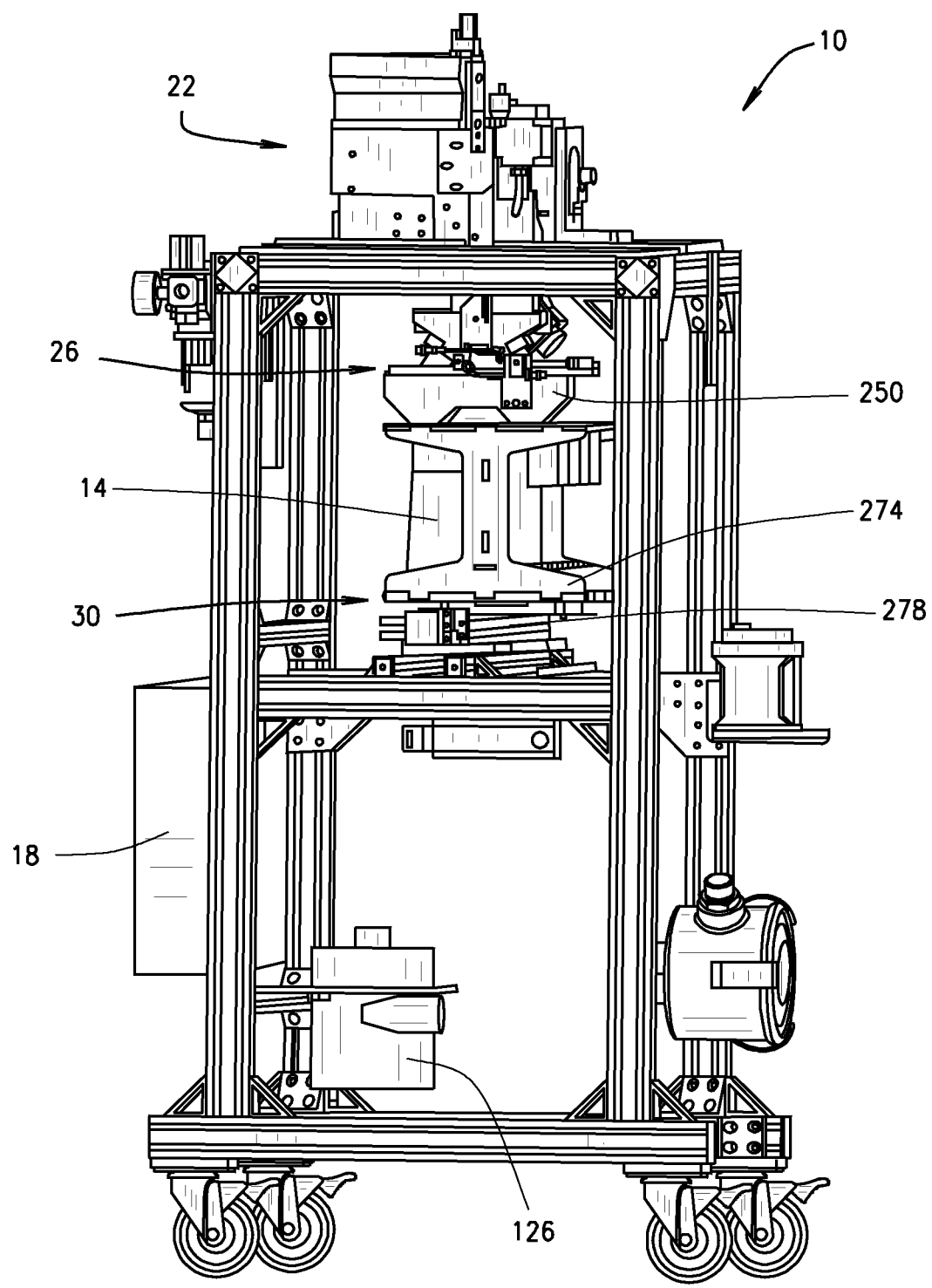
FIG. 1 is an isometric view of a small object counting system, in accordance with various embodiments of the present disclosure.

The following description is merely exemplary in nature and is in no way intended to limit the present teachings, application, or uses. Throughout this specification, like reference numerals will be used to refer to like elements.

FIG. 1 is an isometric view of a small object counting system 10 structured and operable to singulate a plurality of small objects, e.g., seeds, from a large volume of the objects, count the singulated objects and deposit groups of the singulated objects into a plurality of object collection receptacles 14, wherein each group comprises a respective predetermined number of objects to be deposited into the respective receptacle 14. More particularly, the system 10 is an automated system that singulates the objects from the large volume of objects and deposits the respective predetermined number of objects into each of the receptacles 14 in accordance with quantities programmed, i.e., input and stored, into a computer based master control system 18. Thus, each receptacle 14 can receive a different number of objects based on the particular quantity programmed into the master control system 18 for each respective receptacle 14. Moreover, the system 10 is structured and operable to sequentially deposit the respective number of objects into each of the plurality, e.g., four, six, eight, ten or more, of receptacles 14 without interruption to the operation of the system 10.

The small objects singulated, counted and sorted by the system 10 can comprise any type of small object in which it is desirable to rapidly count the objects, parse them in to a plurality of groups of different quantities and sort each group to a particular corresponding one of a plurality of receptacles or containers without interrupting operation of the system 10. For example, in various embodiments, the small objects can be objects, while in other embodiments, the small objects can be ball bearings, small candies, coins, nuts, bolts, washers, screws, nails, tacks or any other suitable small object.

As used herein, the term 'singulate' means to automatically, e.g., robotically, sequentially separate objects one-at-a-time from a plurality of objects. The plurality of objects can include any number of objects greater than one. That is, the plurality of objects can include any number of objects from several or numerous objects, i.e., more than a single object, to a large volume of objects, i.e., a bulk quantity of the objects.

It should be understood that the various embodiments of the small object counting system 10, exemplarily illustrated and described herein, include various braces, beams, platforms, pedestals, stands, etc., to which various components, devices, mechanisms, systems, subsystems, assemblies and sub-assemblies described herein are coupled, connected and/or mounted. Although such braces, beams, platforms, pedestals, stands, etc., are necessary to the construction of various embodiments of the small object counting system 10, description of their placement, orientation and interconnections are not necessary for one skilled in the art to easily and fully comprehend the structure, function and operation of the various embodiments of the small object counting system 10. Moreover, such braces, beams, platforms, pedestals, stands, etc., are clearly illustrated in various figures and, as such, their placement, orientation and interconnections are easily understood by one skilled in the art. Therefore, for simplicity, such braces, beams, platforms, pedestals, stands, etc., will be referred to herein merely as system support structures, absent further description of their placement, orientation and interconnections.

Figure 12:
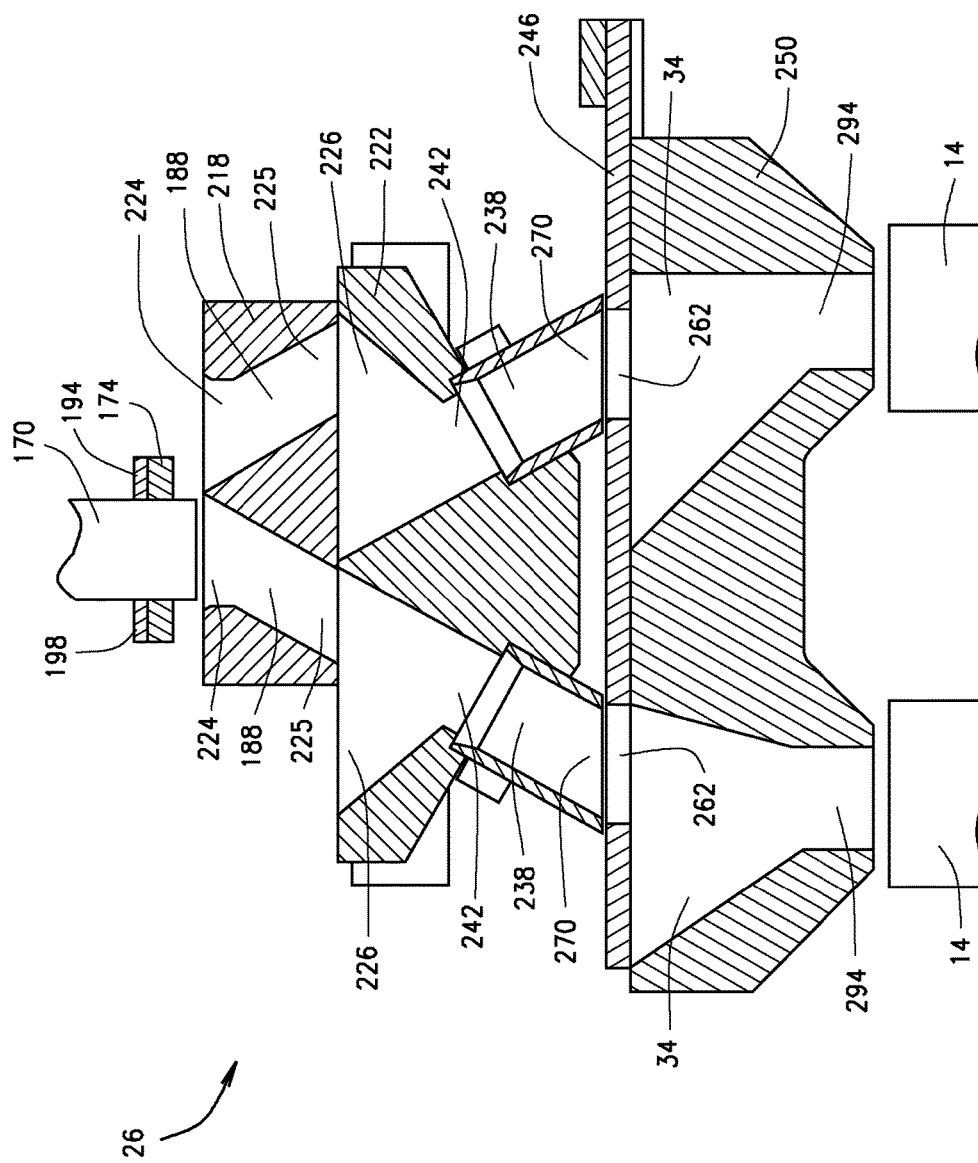
FIG. 12 is cross-sectional view, along line F-F, of the diverter and accumulator module, shown in FIG. 9, having a sluice plate in an object discharge position, in accordance with various embodiments of the present disclosure.
Figure 13:
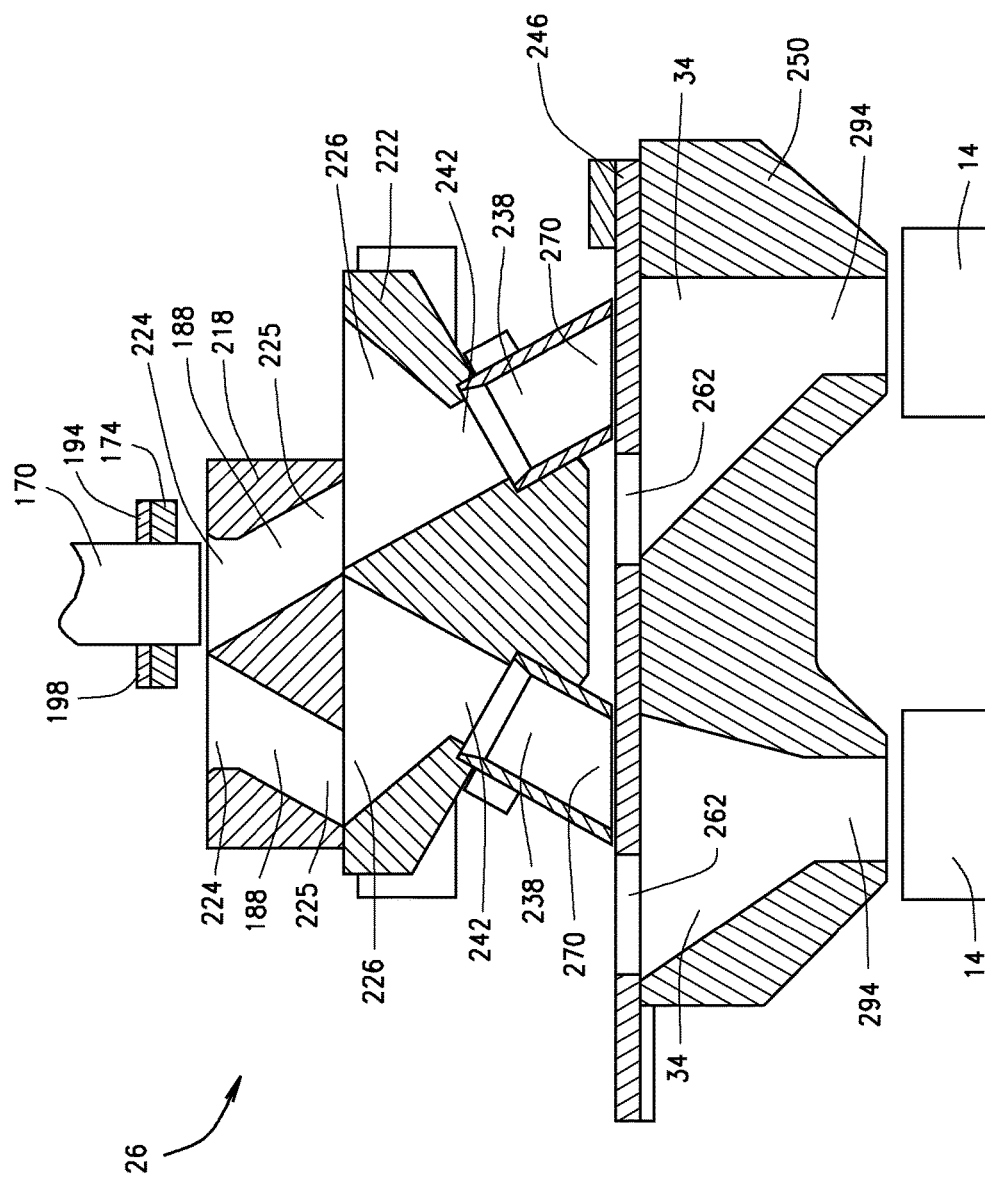
FIG. 13 is cross-sectional view, along line F-F, of the diverter and accumulator module, shown in FIG. 9, having the sluice plate in an object accumulation position, in accordance with various embodiments of the present disclosure.
Figure 14:
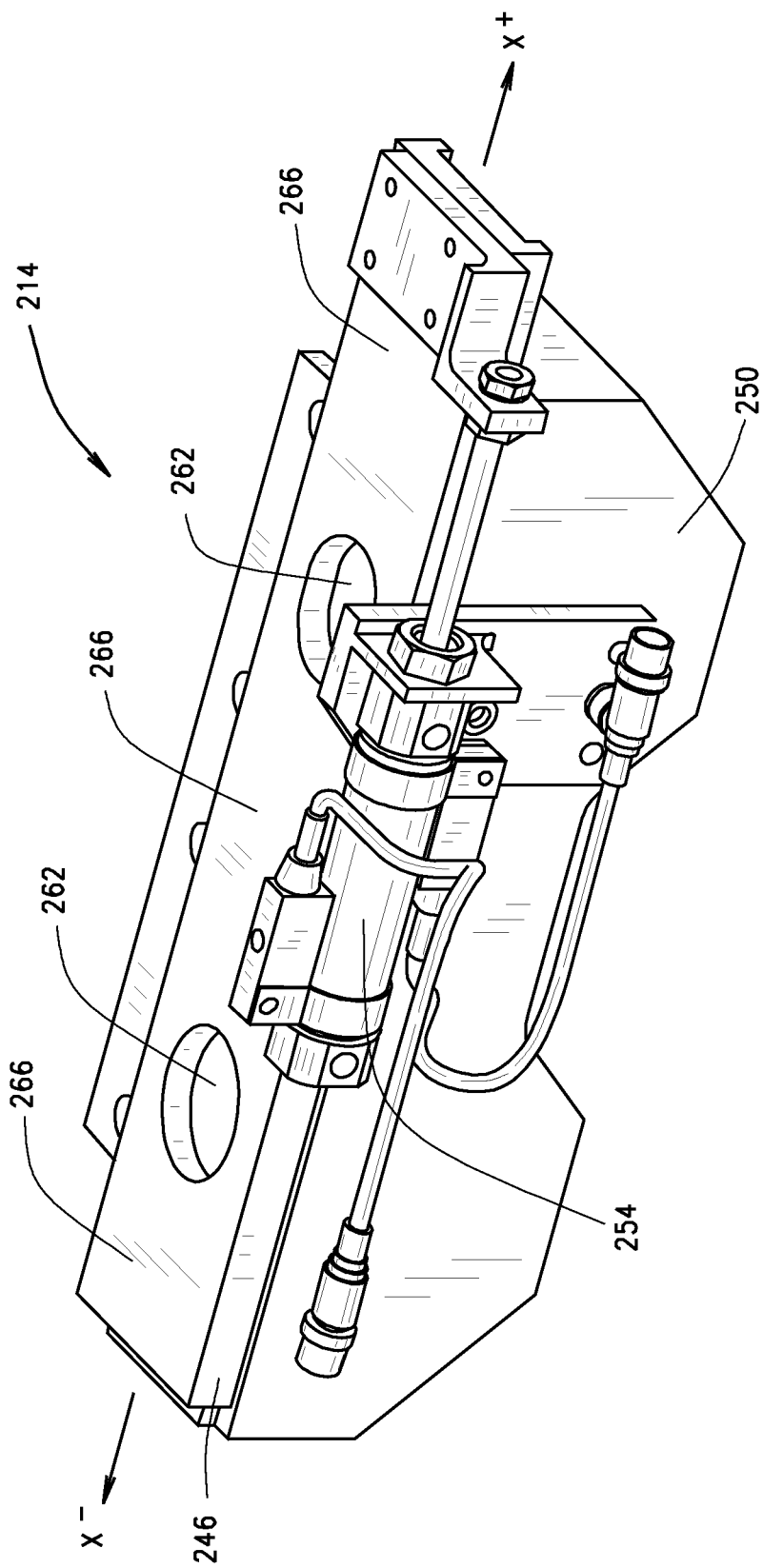
FIG. 14 is an isometric view of an accumulator unit included in the diverter and accumulator module shown in FIG. 9, in accordance with various embodiments of the present disclosure.
Figure 15:
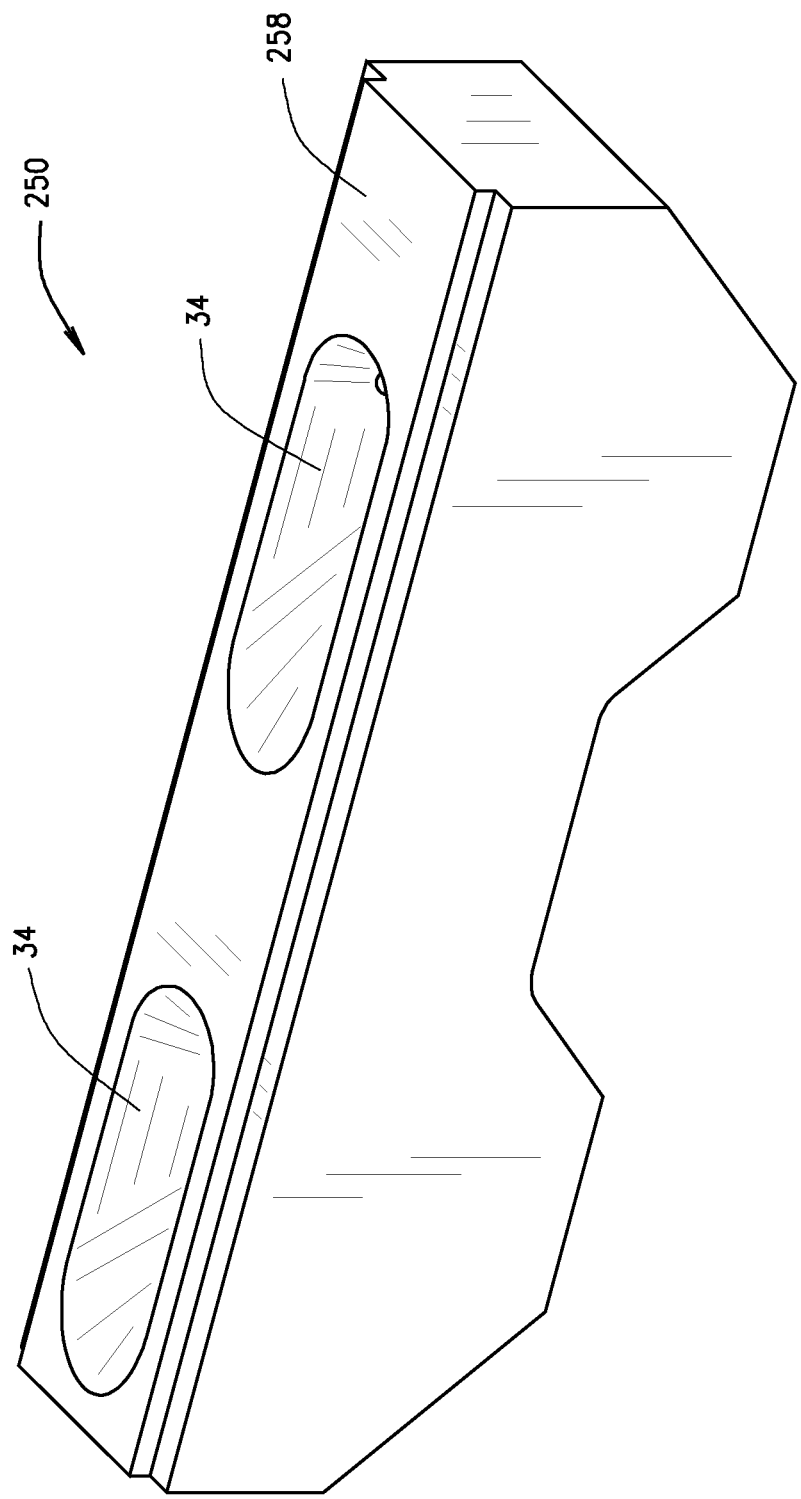
FIG. 15 is an isometric view of a base of the accumulator unit shown in FIG. 14, in accordance with various embodiments of the present disclosure.

The small object counting system 10 includes a singulating and counting (S&C) module 22, a diverter and accumulator (D&A) module 26, an objection collection (OC) module 30 and a computer based master control system 18. Generally, the S&C module 22 is structured and operable to singulate objects from a large volume of the objects and count the singulated objects. The D&A module 26 is structured and operable to sequentially receive the singulated objects, sequentially separate the received objects into groups of objects and direct each group of singulated objects into a selected one of a plurality of discharge funnels 34 (shown in FIGS. 12, 13 and 15) of the D&A module 26. And, the object collection module 30 is structured and operable to automatically, e.g., robotically, sequentially position each one of the object collection receptacles 14 adjacent the discharge funnels 34 such that each group of objects is deposited into a respective corresponding one of the object collection receptacles 14. More particularly, the computer based master control system 18 is operable to control and coordinate the operations of the S&C module 22, the D&A module 26 and the OC module 30 to deposit the programmed number of objects into each of the respective corresponding object collection receptacles 14.

For example, in various embodiments, the master controller 18 controls the operation of the D&A module 26 such that each group of singulated objects comprises an automatically controlled number of objects, wherein at least one of the groups of objects comprises a different number of objects than at least one other group of objects. Additionally, as used herein, the phrase 'group of objects' or 'group of singulated objects' means a programmed number of objects parsed from a plurality of singulated of objects. That is, as described below, the objects are singulated from a large volume of objects by the S&C module 22 and subsequently parsed, or separated, into groups of objects by the D&A module 26 such that each group of objects comprises a respective number, or quantity, of objects that can be different from one or more of the other groups of objects.

Figure 2:
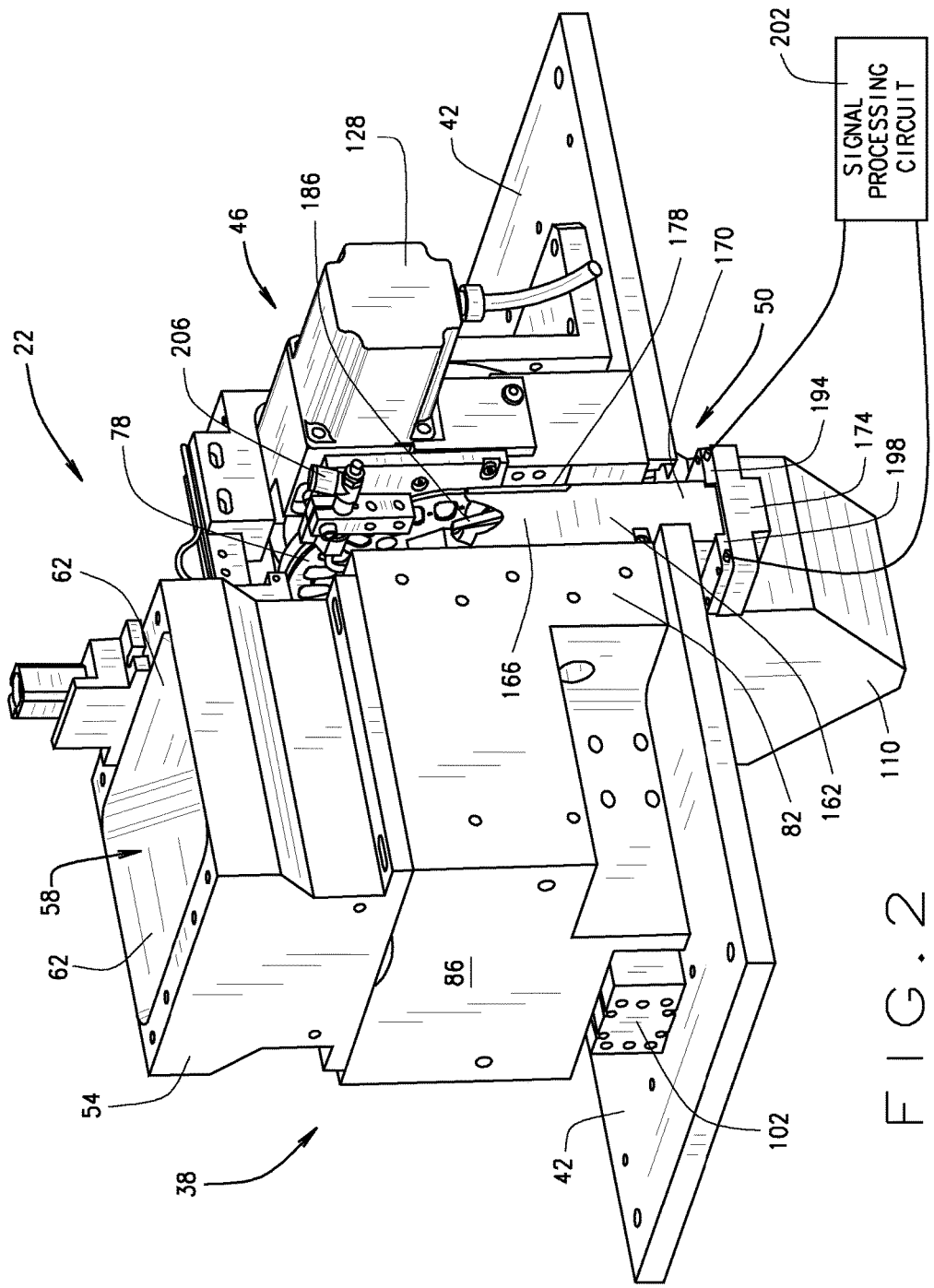
FIG. 2 is an isometric view of a singulating and counting module included in the small object counting system shown in FIG. 1, in accordance with various embodiments of the present disclosure.
Figure 3:
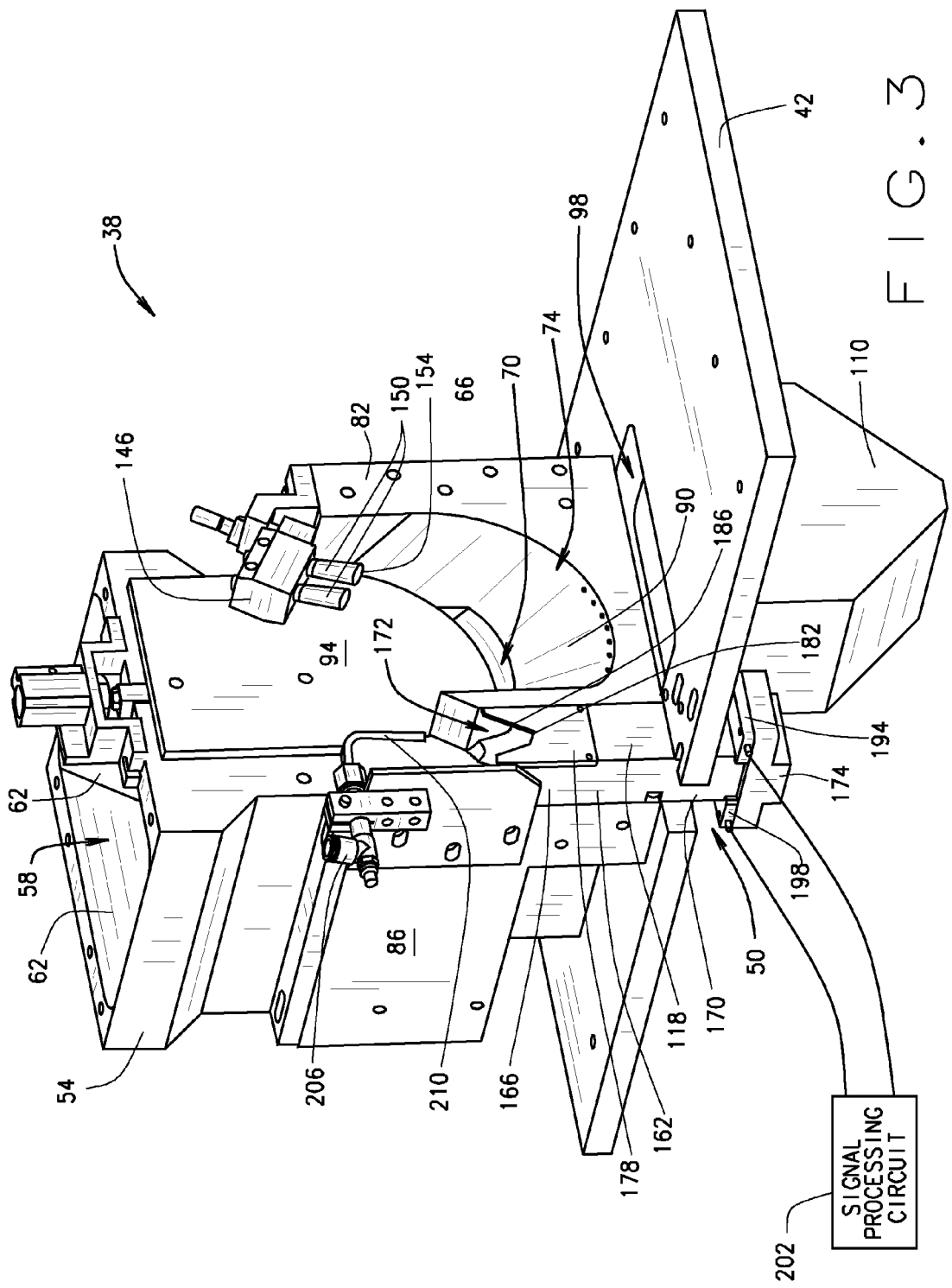
FIG. 3 is an isometric view of a bulk object hopper unit and an object off-load and counting device included in the singulating and counting module shown in FIG. 2, in accordance with various embodiments of the present disclosure.
Figure 4:
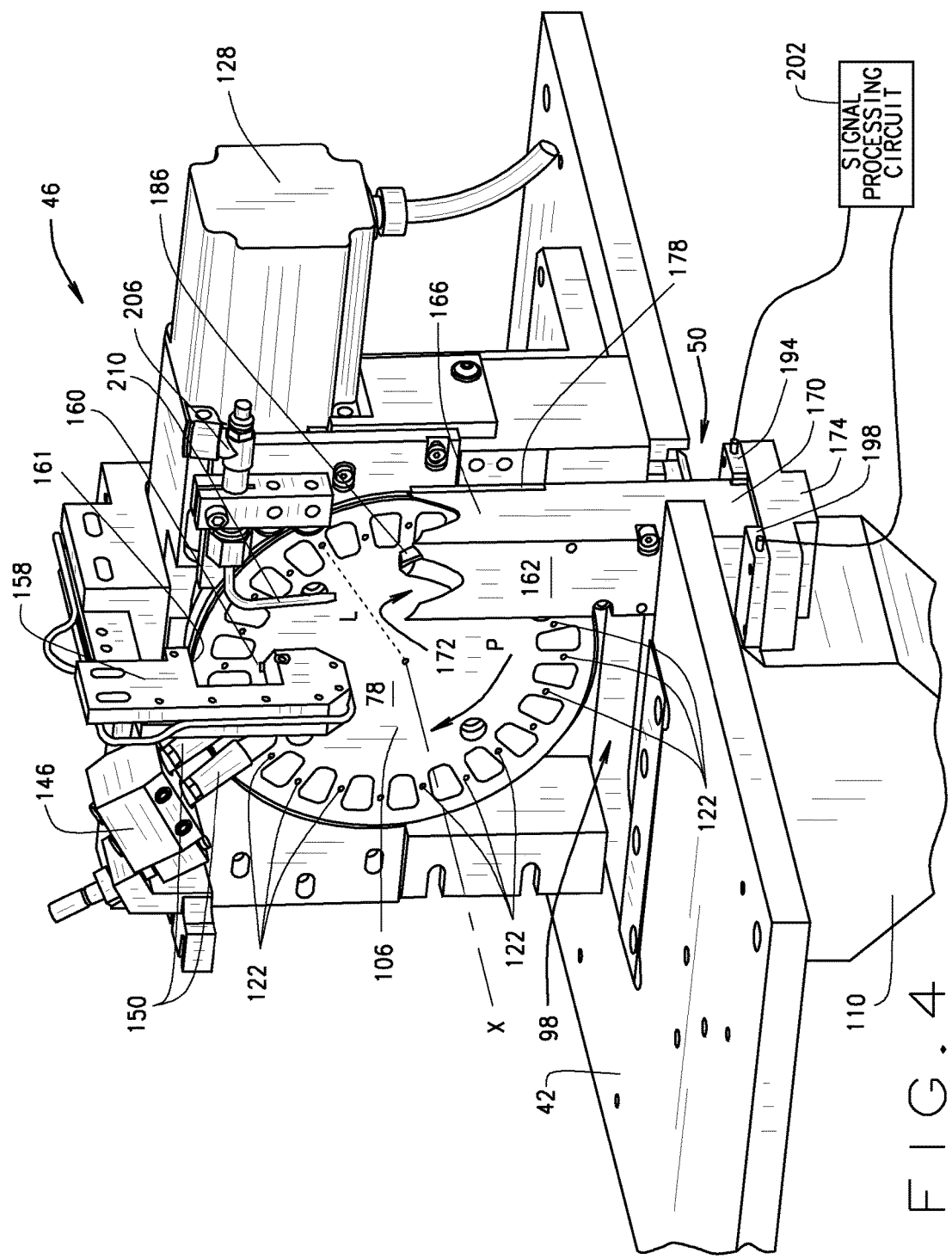
FIG. 4 is an isometric view of a singulating vacuum wheel unit included in the singulating and counting module shown in FIG. 2, in accordance with various embodiments of the present disclosure.

Referring now to FIGS. 2, 3 and 4, in various embodiments the singulating and counting module 22 includes a bulk object hopper unit 38 mounted to a singulating and counting (S&C) module platform 42, a singulating vacuum wheel unit 46 mounted to the S&C module platform 42 adjacent the bulk object hopper unit 38, and an object off-load and counting (O&C) device 50 positioned between the object bulk hopper unit 38 and the singulating vacuum wheel unit 46. The bulk object hopper unit 38 includes an object hopper 54 structured to retain a large volume of objects. For example, in various implementations, the object hopper 54 can be structured to retain 100, 300, 500, 1000 or more objects. The object hopper 54 includes a reservoir 58 having one or more sidewalls 62 that taper downward in a funnel fashion to a bottom 66 angled downward to an object egress opening 70 formed in the sidewall 62 of the reservoir adjacent the singulating vacuum wheel unit 46.

The angle and/or contour of the hopper sidewalls 62 and bottom 66 allow gravitational force to move the objects deposited into the hopper reservoir 58 toward and through the object egress opening 70 into an object singulation chamber 74 formed between the hopper 54 and a singulating vacuum wheel 78 of the singulating vacuum wheel unit 46. Objects flowing, or moving, from the hopper reservoir 58 to the object singulation chamber 74, via the egress opening 70, are then presented to the singulating vacuum wheel 78 for singulation. The object singulation chamber 74 is formed by a generally U-shaped mouth 82 of a base 86 of the bulk object hopper unit 38 that extends beyond the egress opening 70. More particularly, the singulation chamber 74 is formed within the U-shaped mouth 82 between the object hopper 54 and the singulating vacuum wheel 78. The U-shaped mouth 82 includes a bottom 90 that is angled, or canted, downward from the egress opening 70 to the singulating vacuum wheel 78. Thus, objects moving from the hopper reservoir 58 and through the egress opening 70 will move down the U-shaped mouth bottom 90, via gravitational force, and accumulate against, i.e., be presented to, the singulating vacuum wheel 78 where the objects can be singulated, as described below.

In various embodiments, the bulk object hopper unit 38 additionally includes an object baffle 94 adjustably mounted to the exterior of the object hopper 54 above the egress opening 70. The object baffle 94 is adjustably mounted to the object hopper 54 such that the baffle 94 can be moved to adjust the size of the egress opening 70, thereby controlling the amount of objects that accumulate within the singulation chamber 74. Moreover, by controlling the amount of objects that accumulate within the singulation chamber 74, the pressure exerted on each object and/or the singulating vacuum wheel 78 by the weight of the surrounding objects can be controlled. Particularly, pressure exerted on a plurality of contacting objects, i.e., objects in contact with each other and/or the singulating vacuum wheel 78, can be controlled so as to reduce or eliminate 'bridging', i.e., interlocking, of contacting objects. That is, if too many objects accumulate within the singulation chamber 74, the force exerted on each object and/or the singulating vacuum wheel 78, particularly the objects closer to the bottom 90 of the U-shaped mouth 82, by the surrounding objects can cause two or more objects to bridge, or interlock, such that the objects can not be extracted by the singulation vacuum wheel 78, as described below.

In various forms, the object baffle 94 can be manually adjustable to increase the size of the egress opening 70 to allow more objects to accumulate within the singulation chamber 74, or decrease the size of the egress opening 70 to reduce the number objects allowed to accumulate within the singulation chamber 74. In other embodiments, the object baffle 94 can be controlled by the master control system 18 to automatically increase the size of the egress opening 70 to allow more objects to accumulate within the singulation chamber 74, or decrease the size of the egress opening 70 to reduce the number objects allowed to accumulate within the singulation chamber 74.

Referring now to FIGS. 2, 3, 4 and 5, in various embodiments, the S&C module 22 includes a hopper evacuation opening 98 formed in the S&C platform 42. Additionally, in such embodiments, the bulk object hopper unit 38 is mounted to a linear stage 102 coupled to the S&C platform 42. In various implementations, the linear stage 102 is controllable by the master control system 18 to move the bulk object hopper unit 38 between a singulating position (shown in FIG. 2) and an evacuation position (shown in FIG. 5). When placed in the singulating position, the bulk object hopper unit 38, particularly the U-shaped mouth 82, will cover the hopper evacuation opening 98 and be in very close proximity to a face 106 of the singulating vacuum wheel 78. Therefore, when placed in the singulating position, all objects are retained within the hopper reservoir 58 and the singulation chamber 74 so that the objects within the singulation chamber 74 can be singulated by the singulating vacuum wheel 78. However, when moved to the evacuation position, the bulk object hopper unit 38, particularly the U-shaped mouth 82, will be moved away from the singulating vacuum wheel unit 46 to expose the evacuation opening 98. Additionally, moving the bulk object hopper unit 38 to the evacuation position breaches or severs the singulation chamber 74 such that the object within the hopper reservoir 58 and the singulation chamber 74 will no longer be retained therein. Thus, due to the angle and/or contour of the hopper reservoir sidewalls 62, hopper reservoir bottom 66 and the singulation chamber bottom 90, gravitational force will cause all the objects within the hopper reservoir 58 and the singulation chamber 74 to fall through the evacuation opening 98. The S&C module 22 additionally includes a hopper evacuation funnel 110 mounted to a bottom side of the S&C platform 42 beneath the hopper evacuation opening 98 for funneling the object into a removable evacuation container (not shown). Thus, when the bulk object hopper unit 38 is moved to the evacuation position, all the objects remaining within the hopper reservoir 58 and singulation chamber 74 will be evacuated through the evacuation opening 98 into the evacuation container.

Figure 5:
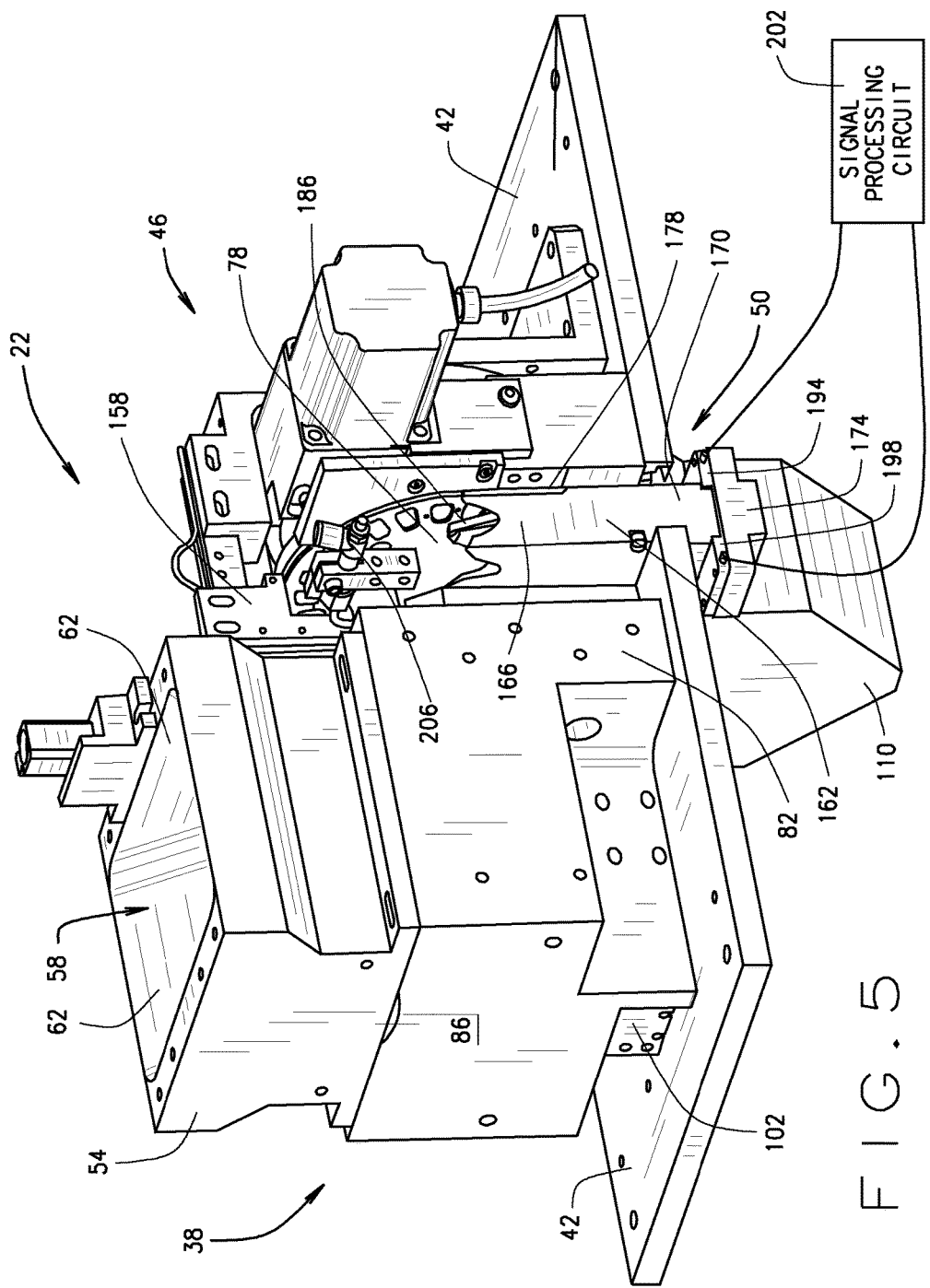
FIG. 5 is an isometric view of the singulating and counting module shown in FIG. 2, illustrating a bulk object hopper unit of the singulating and counting module placed in an object evacuation position, in accordance with various embodiments of the present disclosure.

Referring now to FIGS. 3, 4 and 5, as described above, the singulating vacuum wheel unit 46 includes the singulating vacuum wheel 78 that is operable to singulate, i.e., extract one-at-a-time, objects from a large volume of objects retained within the bulk object hopper 54, and more particularly within the singulation chamber 74. The singulating vacuum wheel 78 is mounted for rotation in a vertical plane such that a portion of the singulating vacuum wheel 78 will be in contact with the objects retained with in the singulation chamber 74. Additionally, the object O&C device 50 is positioned between the object bulk hopper unit 38 and the singulating vacuum wheel unit 46 such that a object stripping side 118 (best shown in FIG. 3) of the object O&C device 50 is planarly parallel with, and in close proximity to, the face 106 of the singulating vacuum wheel 78.

The singulating vacuum wheel 78 includes a plurality of vacuum ports 122 that are circumferentially spaced apart around a perimeter portion of the singulating vacuum wheel 78. That is, as illustrated in FIG. 4, the vacuum ports 122 are substantially equally spaced in a circle and are located radially inward from a perimeter of the singulating vacuum wheel 78. The vacuum ports 122 extend through the singulating vacuum wheel face 106 and are communicatively coupled to a vacuum system 126 (shown in FIG. 1) such that a vacuum can be provided at each of the vacuum ports 122. The singulating vacuum wheel unit 46 additionally includes a motor 128 operable to rotate the singulating vacuum wheel 78 in a P direction about an X axis. During rotation of the singulating vacuum wheel 78, each vacuum port 122 will circularly travel past the object singulation chamber 74, where each vacuum port 122 will extract an object from the singulation chamber 74, and follow a circular path past the object O&C device 50, where each object is removed from the singulating vacuum wheel 78, as described further below.

More specifically, in operation, with objects retained within the singulation chamber 74 and in contact with the singulating vacuum wheel 78, the vacuum system 126 is activated to provide a vacuum to each of the vacuum ports 122 and the motor 128 is activated to rotate the singulating vacuum wheel 78. As the singulating vacuum wheel 78 rotates, each vacuum port 122 travels past the singulating chamber 74. As each vacuum port 122 passes the singulation chamber 74, at least one object is drawn to each vacuum port 122 and retained by the respective vacuum port 122 by the vacuum provided at each vacuum port 122. As the singulating vacuum wheel 78 continues to rotate, each object that has been drawn to a vacuum port 122 is separated from, or extracted from, the plurality of objects within the singulation chamber 74. Each extracted object is then carried around to the object O&C device 50 where each object is removed from the face 106 of the singulating vacuum wheel 78, as described below.

In various embodiments, the singulating vacuum wheel unit 46 is structure to accommodate a plurality of interchangeable singulating vacuum wheels 78. Thus, the singulating vacuum wheel unit 46 can be configured with any one of a plurality of different interchangeable singulating vacuum wheels 78 depending on desired features, properties and/or characteristics of the respective singulating vacuum wheel 78 and the type and/or size of the objects to be singulated. For example, different singulating vacuum wheels 78 can include a different number and/or size, i.e., diameter, of vacuum ports 122 to alter the number of objects that are singulated in a given period of time.

Figure 6:
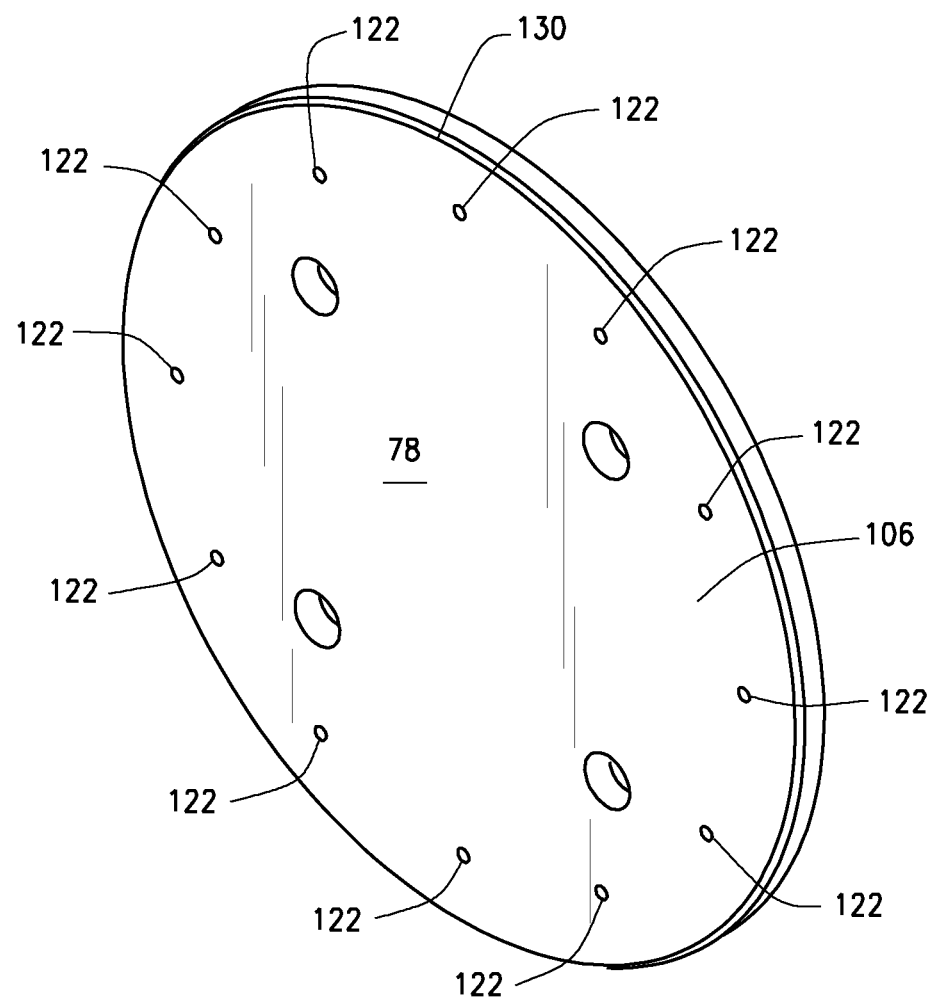
FIG. 6 is an isometric view of a singulating vacuum wheel included in the singulating vacuum wheel unit shown in FIG. 4, in accordance with various embodiments of the present disclosure.
Figure 7:
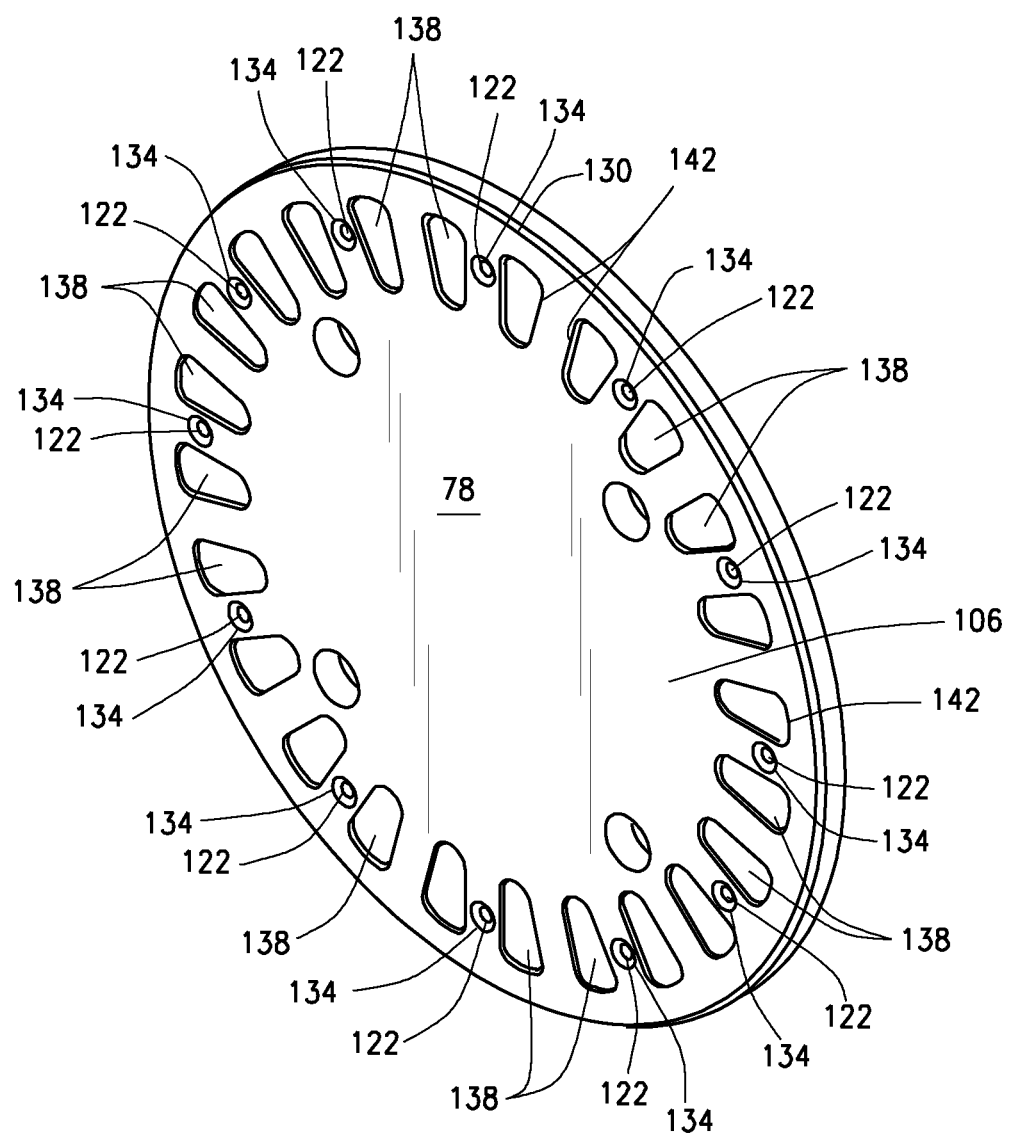
FIG. 7 is an isometric view of a singulating vacuum wheel included in the singulating vacuum wheel unit shown in FIG. 4, in accordance with various other embodiments of the present disclosure.
Figure 8:
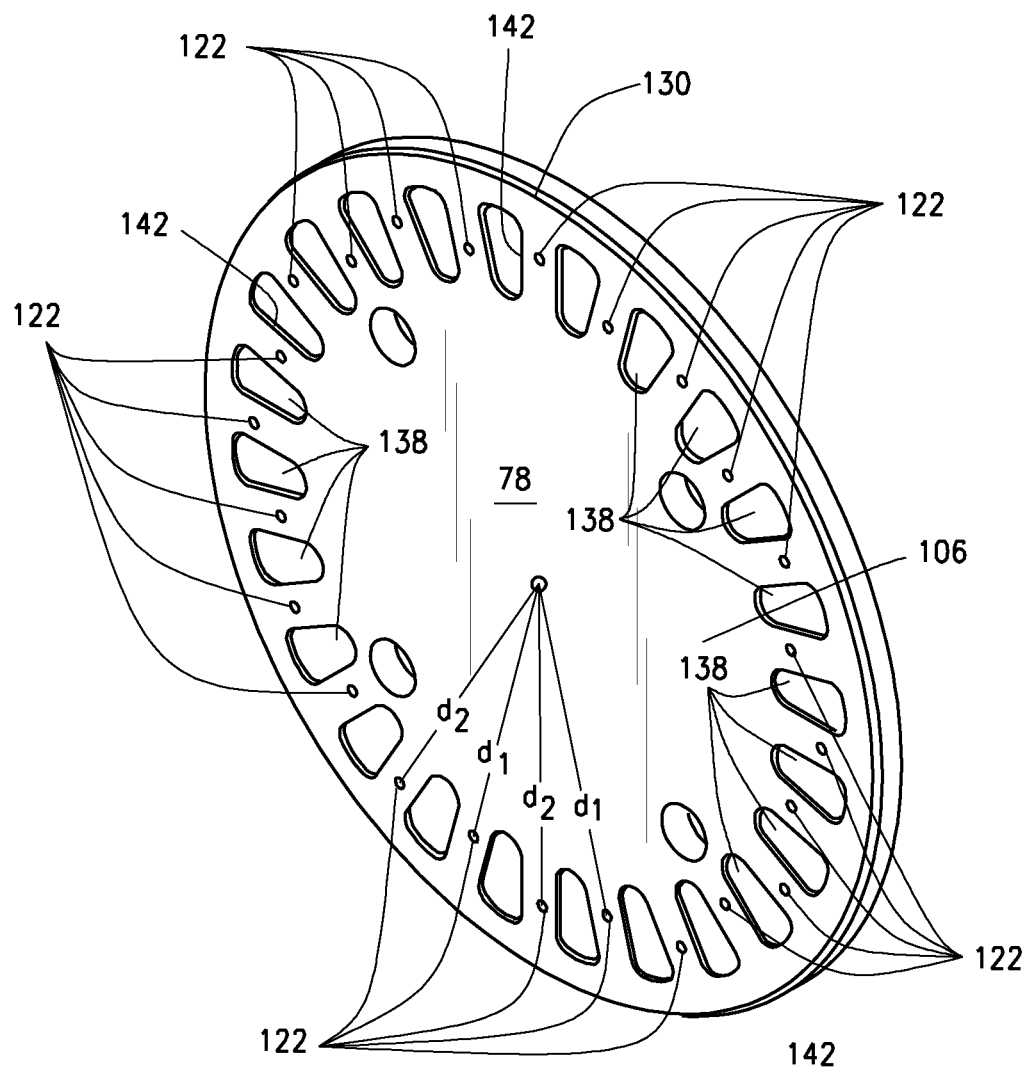
FIG. 8 is an isometric view of a singulating vacuum wheel included in the singulating vacuum wheel unit shown in FIG. 4, in accordance with yet other embodiments of the present disclosure.

Referring now to FIGS. 6, 7 and 8, in various embodiments the face 106 of the singulating vacuum wheel 78 includes a coating 130 having a low coefficient of friction. The coating 130 substantially reduces or eliminates any abrasion to the objects within the singulation chamber 74 by the face 106 during rotation of the singulating vacuum wheel 78. Additionally, the coating 130 substantially resists or prevents debris, dust or particulate matter from sticking to the face 106. The coating can comprise any material suitable for covering the face 106 and having a low coefficient of friction. For example, in various implementations, the coating 130 can comprise a Teflon® anodized finish to significantly lower the coefficient of friction and reduce or eliminate abrasion to the objects, and debris, dust, etc., from sticking to the face 106.

With particular reference to FIG. 6, as described above, in various embodiments, the vacuum ports 122 are substantially equally spaced in a circle located radially inward from a perimeter of the singulating vacuum wheel 78. The size, i.e., diameter, of the vacuum ports 122 can be calculated to provide a particular amount of vacuum flow at each vacuum port 122. Generally, the amount of vacuum provided at each vacuum port 122 is a function of the cumulative cross section of all the vacuum ports 122 in the singulating vacuum wheel 78. Thus, the vacuum ports 122 can be sized to provide more or less vacuum force in accordance the size and/or weight of the objects to be singulated, and in accordance with the number of vacuum ports 122 included in the respective vacuum wheel 78.

With particular reference to FIG. 7, in various embodiments, the face 106 of the singulating vacuum wheel 78 includes a recess 134 at each vacuum port 122 such that each vacuum port 122 is formed as a recessed vacuum port. The recesses 134 allow a portion of singulated objects to protrude into the respective recess 134 such that a larger surface area of each respective object is in contact with the face 106. The larger area of contact for each object with the singulating vacuum wheel face 106 provides a firmer or stronger retention of the each respective object on the face 106, which can improve singulation accuracy, consistency and speed of larger objects.

With particular reference to FIG. 8, in various embodiments, the vacuum ports 122 are formed within the singulating vacuum wheel 78 such that various selected vacuum ports 122 are different radial distances from a center C of the singulating vacuum wheel 78. For example, in various embodiments, the radial distance of the vacuum ports 122 sequentially alternates between a first radial distance d1 and a second radial distance d2. The varying radial distance from the center C of the vacuum ports 122 assists in reducing or eliminating 'bridging', i.e., interlocking, of contacting objects within the singulation chamber 74 by extracting objects from different areas or level within the singulation chamber 74.

With particular reference to FIGS. 7 and 8, in various embodiments, the face 106 of the singulating vacuum wheel 78 includes a plurality of shallow object agitating cavities 138. The object agitating cavities 138 are structured to agitate or disrupt the location and/or orientation of various objects within the singulation camber 74 as the singulating vacuum wheel 78 rotates. More particularly, as the singulating vacuum wheel 78 rotates through the singulation chamber 74, objects within the singulation chamber 74 will move or reorient slightly, i.e., fall into the agitating cavities 138, due to the weight or force of the surrounding objects and the void created by each agitating cavity 138. Then, as the singulating vacuum wheel 78 continues to rotate and move the agitating cavities 138 through the singulation chamber 74 a perimeter edge 142 of each agitating cavity 138 will again move or reorient, i.e., agitate, objects within the singulation chamber 74. Agitating the objects within the singulation chamber 74 assist in reducing or eliminating 'bridging', i.e., interlocking, of contacting objects within the singulation chamber 74. The agitating cavities 138 can have any depth suitable to agitate the objects within the singulation chamber 74 to assist in reducing or eliminating 'bridging' of objects within the singulation chamber 74. For example, the agitating cavities 138 can have a depth between approximately 0.010 inches and 0.050 inches, e.g., 0.030 inches. Additionally, in various embodiments, the perimeter edge 142 of each agitating cavity 138 is chamfered, or beveled, to agitate the objects without damaging or abrading the objects.

Referring now to FIGS. 3 and 4, in various implementations, the bulk hopper unit 38 can include an excess object removal device 146 that is structured and operable to dislodge at least one of a plurality of objects drawn to and extracted by any of the vacuum ports 122. More particularly, the excess object removal device 146 dislodges, i.e., removes, excess objects, i.e., objects greater than one, from the face 106 of the singulating vacuum wheel 78 that occasionally may be extracted from the singulation chamber 74 by any one of the vacuum ports 122. Therefore, each respective object vacuum port 122 will retain only a single object to the face 106 of the singulating vacuum wheel 78 as each respective object is carried toward the object O&C device 50. The excess object removal device 146 can be any device suitable for removing objects in excess of a single object from any of the vacuum ports 122.

For example, in various embodiments, the excess object removal device 146 can comprise at least one brush 150 positioned adjacent the face 106 of the singulating vacuum wheel 78. In such embodiments, the at least one brush 150 is position adjacent the face 106 such that, in the instance where a particular vacuum port 122 has extracted more than a single object, e.g., two objects, from the singulation chamber 74, the at least one brush 150 will contact the extraneous, or extra, object(s) and dislodge it/them from the face 106. As used herein, the extraneous, or extra, object(s) are the object(s) that are not directly in contact with the respective vacuum port 122, or put another way, the object(s) that are not substantially centered on the respective vacuum port 122. The single object that is substantially centered, e.g., directly in contact with the respective vacuum port 122, is referred to herein as the primary object. The extraneous, or extra, object(s) will generally extend radially outward, i.e., further away from the center C, than the primary objects. Therefore, as the singulating vacuum wheel 78 carries the respective primary and extraneous objects out of the singulation chamber 74 toward the object O&C device 50, the at least one brush 150 will contact the extraneous object(s), while not contacting with the primary object, and dislodge, i.e., remove, the extraneous object(s) from the singulating vacuum wheel face 106. The dislodged object(s) will the fall back into the singulation chamber 74.

Additionally, in various embodiments, the excess object removal device 146 can include a pair of brushes 150, wherein one of the brushes 150, i.e., a 'removal' brush 150, is located adjacent the face 106 of the singulating vacuum wheel 78 to dislodge or remove extraneous object(s) retained by any single vacuum port 122, as described above. And, the other brush 150, i.e., a 'reorientation' brush 150, is located adjacent the face 106 to reorient the objects on the singulating vacuum wheel face 106. More particularly, the reorientation brush 150 can be located so that a distal end 154 is located radially outward from the vacuum ports 122, i.e., having a radial distance from the center C that is greater than the radial distance from the center C of the vacuum ports 122. Therefore, as the singulating vacuum wheel 78 rotates, the reorientation brush 150 will contact and reorient non-circular and/or non-spherical objects, e.g., oblong, oval, rectangular, triangular, etc., such that a longitudinal axis of the object is aligned approximately orthogonally with a radial line L (shown as a dashed line in FIG. 4) extending from the center C of the face 106 to the respective vacuum port 122.

More specifically, non-circular and/or non-spherical objects that are extracted from the singulation chamber 74 may be extracted being oriented on the face 106 with the longitudinal axis of the respective object significantly skewed from being approximately orthogonal with the radial line L. In such instances, as the singulating vacuum wheel 78 carries the respective object past the reorientation brush 150, the reorientation brush 150 will contact the most radially outward extending end or portion of the object. As the reorientation brush 150 contacts the most radially outward extending end or portion of the respective object, the object will be turned, spun or rotated on the face 106 so that the longitudinal axis of the respective object is approximately orthogonal with the radial line L.

Referring particularly to FIG. 4, in various embodiments, the bulk hopper unit 38 can include a single object verification sensor 158 operable to determine whether each vacuum port 122 is carrying only a single object to the object O&C device 50. The object verification sensor 158 is located adjacent the face 106 of the singulating vacuum wheel 78, and more particularly, adjacent the vacuum ports 122, such that each object will pass the object verification sensor 158 as each respective object is carried from the singulation chamber 74 toward the object O&C device 50. The single object verification sensor 158 can be any sensor capable of communicating with the master control system 18 and suitable for determining whether each respective vacuum port 122 is transporting only a single object toward the object O&C device 50, or more particularly, determining whether any vacuum port 122 is transporting two or more objects toward the object O&C device 50. For example, in various implementations, the single object verification sensor 158 comprises a photoelectric sensor including an emitter 160 that emits an optic signal and a receiver 161 that receives the optic signal. The optic signal is emitted parallel to the face 106 of the singulating vacuum wheel 78 and across a portion of the circular path the objects will travel between the singulation chamber 74 and the object O&C device 50. Therefore, as each vacuum port 122 passes adjacent the single object verification sensor 158, the object(s) retained by each respective vacuum port 122 will pass between the emitter 160 and receiver 161 breaking, i.e., blocking, the optic signal. The single object verification device 158 communicates with the master control system 18 to determine whether the length of time the optical signal is blocked as each vacuum port 122 passes adjacent the single object verification sensor 158 is indicative of a single object or multiple objects. In various embodiments, if multiple objects are sensed, the master control system 18 can stop rotation of the singulating vacuum wheel 78 so that the multiple objects can be removed or reverse the direction of rotation of the singulating vacuum wheel 78 to allow the excess object removal device 146 to dislodge the extraneous objects, as described above.

Referring now to FIGS. 2, 3, 4 and 5, in various embodiments, the object O&C device 50 includes a hollow tubular body 162 having a top portion 166 extending above the singulating and counting module platform 42, a bottom portion 170 extending below the singulating and counting module platform 42, and a center bore 172 extending the length of the body 162. The object O&C device 50 additionally includes a counting device 174 mounted to a distal end of the bottom portion 170, and a stripping plate 178 comprising a distal portion of the object stripping side 118. As described above, the object O&C device 50 is positioned between the object bulk hopper unit 38 and the singulating vacuum wheel unit 46 such that the object stripping side 118 is in close proximity to the face 106 of the singulating vacuum wheel 78. More particularly, the object O&C device 50 is positioned to have the object stripping plate 178 planarly parallel with, and in close proximity to, the face 106 of the singulating vacuum wheel 78. For example, in various implementations, the object stripping plate 178 can be positioned within approximately 0.010 to 0.030 inches of the face 106. Still more particularly, the object O&C device 50 is positioned so that as the singulating vacuum wheel 78 rotates, each extracted object will contact the stripping plate 178 causing each extracted object to be physically dislodged from the face 106 of the singulating vacuum wheel 78 and fall into the tubular body center bore 172.

In various embodiments, the object stripping plate 178 includes a substantially V-shaped leading edge 182 (best shown in FIG. 3) that is chamfered inward (as best shown in FIG. 2) toward the center bore 172 of the tubular body 162. In such embodiments, the object O&C device 50 is positioned so that as the singulating vacuum wheel 78 rotates, each extracted object will contact a first side 186 of the substantially V-shaped leading edge 182. Subsequently, as the singulating vacuum wheel 78 continues to rotate, each extracted object will be pushed radially outward from the respective vacuum port 122 by the leading edge 182 and becomes physically dislodged from the respective vacuum port 122. Each dislodged object will fall into and travel through the tubular body center bore 172 into one of a plurality of diverting channels 188 of a diverter unit 190 (shown in FIGS. 9 and 10) of the D&A module 26.

In various embodiments, in addition to each object being physically dislodged by the object stripping plate 178, each object can be released from respective vacuum 122 port by temporarily terminating the vacuum at each individual vacuum port 122 as the respective object approaches the object stripping plate 178. In other embodiments, each object can be blown from the respective vacuum port 122 by temporarily providing forced air at each individual vacuum port 122 as the respective object approaches the object stripping plate 178.

As each dislodged object travels from the bottom portion 170 of the object O&C device tubular body 162 into one of the diverting channels 188, each object will pass the counting device 174 to be counted. More particularly, the counting device 174 is communicatively coupled to the master control system 18 and sends a corresponding pulse, or signal, to the master control system 18 as each dislodged object passes the counting device 174. The master control system 18 counts the pulses, or signals, and based on the counted pulses, controls the operation of the D&A module 26 and the OC module 30 to parse the objects into the plurality of groups and sort each group to the particular corresponding one of the collection receptacles 14. Specifically, the counting device 174 sends a corresponding signal to the master control system 18 as each object passes the counting device 174, and substantially, simultaneously, the master control system 18 counts the signals and compares the count with programmed number of objects to be included in a respective group of singulated objects, e.g., a number stored in an electronic spreadsheet or database. Then based on the comparison, the master control system 18 controls and coordinates the operations of the S&C module 22, the D&A module 26 and the OC module 30 to deposit the programmed number of objects, e.g., the number of objects as stipulated by the electronic spreadsheet or database, into the respective corresponding object collection receptacle 14.

It should be understood that, in various embodiments, the master control system 18 continuously rotates the singulating vacuum wheel 78 to provide a substantially steady stream of objects being counted and funneled into the diverter channels 188. Substantially simultaneously, the master control system 18, controls and coordinates the operations of the D&A module 26 and the OC module 30 to parse the objects into the plurality of groups and sort each group to the particular corresponding one of the collection receptacles 14. Generally, during operation of the small object counting system 10, the master control system 18 only stops rotation of the singulating vacuum wheel 78 after each of the collection receptacles 14 has received the respective number, i.e., group, of objects, or when the system 10 encounters an error or malfunctions. However, the master control system 18 can control the rotational speed of the singulating vacuum wheel 78 to control the speed at which the objects are extracted from singulation chamber 74 and funneled into the diverter unit 190.

The counting device 174 can be any device suitable for counting each object as it travels from the tubular body 162 into the diverting unit 190. For example, in various embodiments, the counting device 174 can be a photoelectric sensor comprising a transmitter 194 that emits one or more optic beams, or signals, across the distal end of the tubular body bottom portion 170 to a receiver 198. In such embodiments, each object will break the optic beam(s) as each respective object travels past the counting device 174. Each time the optic beam(s) is/are broken by a passing object, the counting device 174 will send a pulse, or signal, to the master control system 18 that counts, accumulates or registers the pulses to track the number of objects passing the counting device 174. Then, as described above, the master control system 18 compares the counts with programmed numbers of objects to be included in each respective group of singulated objects, and controls and coordinates the operations of the D&A module 26 and the OC module 30 to deposit the programmed number of objects into the respective corresponding object collection receptacle 14.

Furthermore, in various embodiments, the photoelectric sensor counting device 174 comprises a bypass filter wherein the transmitter 194 emits an array of optic signals, or beams, received by the receiver 198. The receiver 198 sends an analog signal to a signal processing circuit 202 that measures the level of intensity of the light emitted by each optic signal. As an object passes the counting device 174 the object will interfere with the optic signals causing a variance in the intensity. The signal processing circuit 202 monitors the intensity of the optic signals and when a variance in the intensity exceeds a predetermined threshold, or trigger limit, indicative of an object passing the counting device 174, the signal processing circuit 202 sends a digital signal, or pulse, to the master control system 18. Subsequently, as described above, the master control system 18 counts the signals and compares the count with the programmed number of objects to be included in each respective group of singulated objects, and controls and coordinates the operations of the D&A module 26 and the OC module 30 to deposit the programmed number of objects into the respective corresponding object collection receptacle 14.

In various embodiments, the bulk object hopper unit 38 further includes a forced air object travel assist device 206 mounted above the object O&C device tubular body 162. The forced air object travel assist device 206 is connected to a forced air supply (not shown) includes an air nozzle 210 that pointed into the tubular body center bore 172. The master control system 18 controls a flow of forced air supplied to the forced air object travel assist device 206 to inject a stream of air into the tubular body center bore 172. The stream of forced air will assist the travel of each dislodged object through the tubular body into the diverter unit 190.

Figure 9:
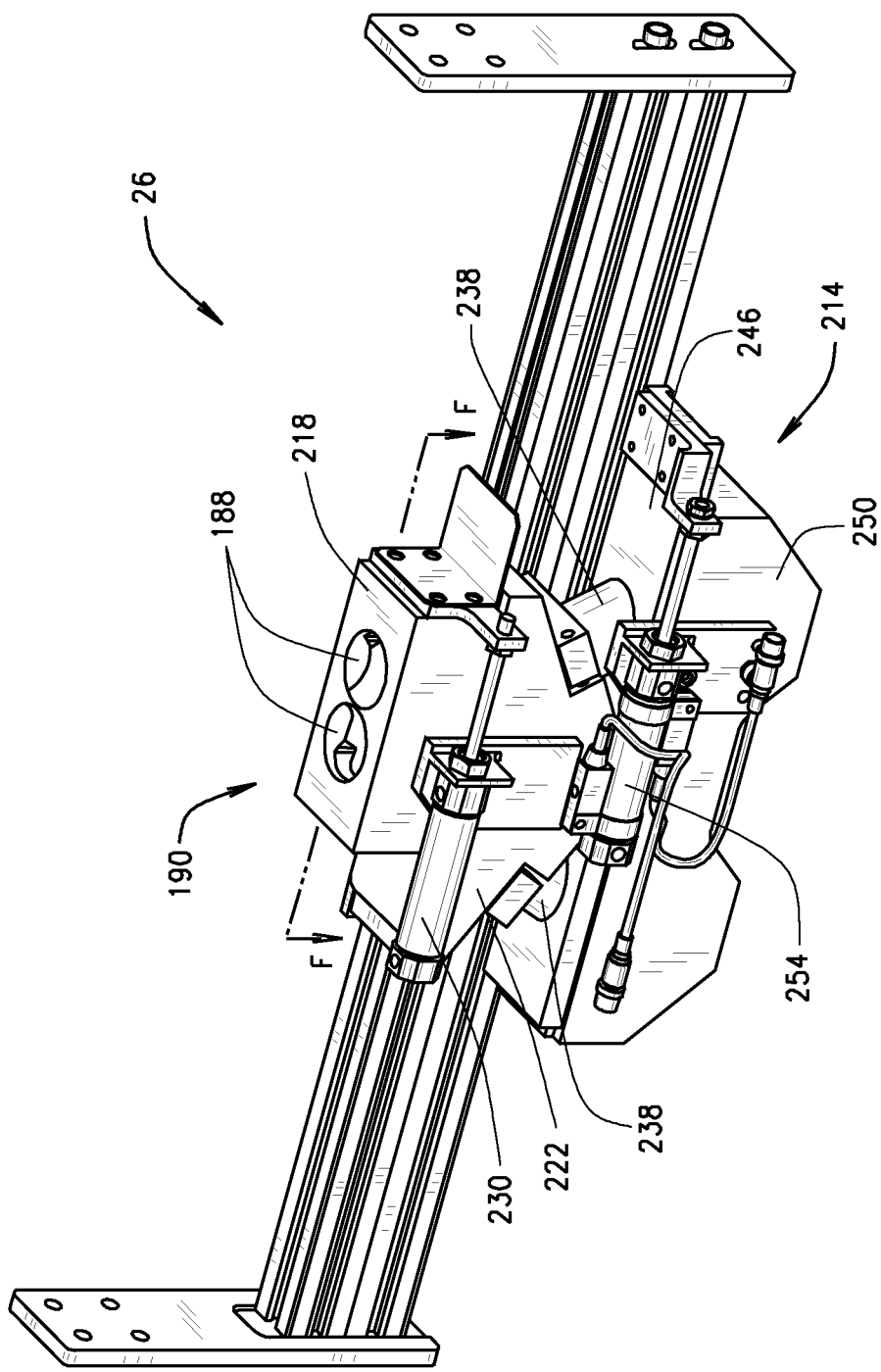
FIG. 9 is an isometric view of a diverter and accumulator module included in the small object counting system shown in FIG. 1, in accordance with various embodiments of the present disclosure.
Figure 10:
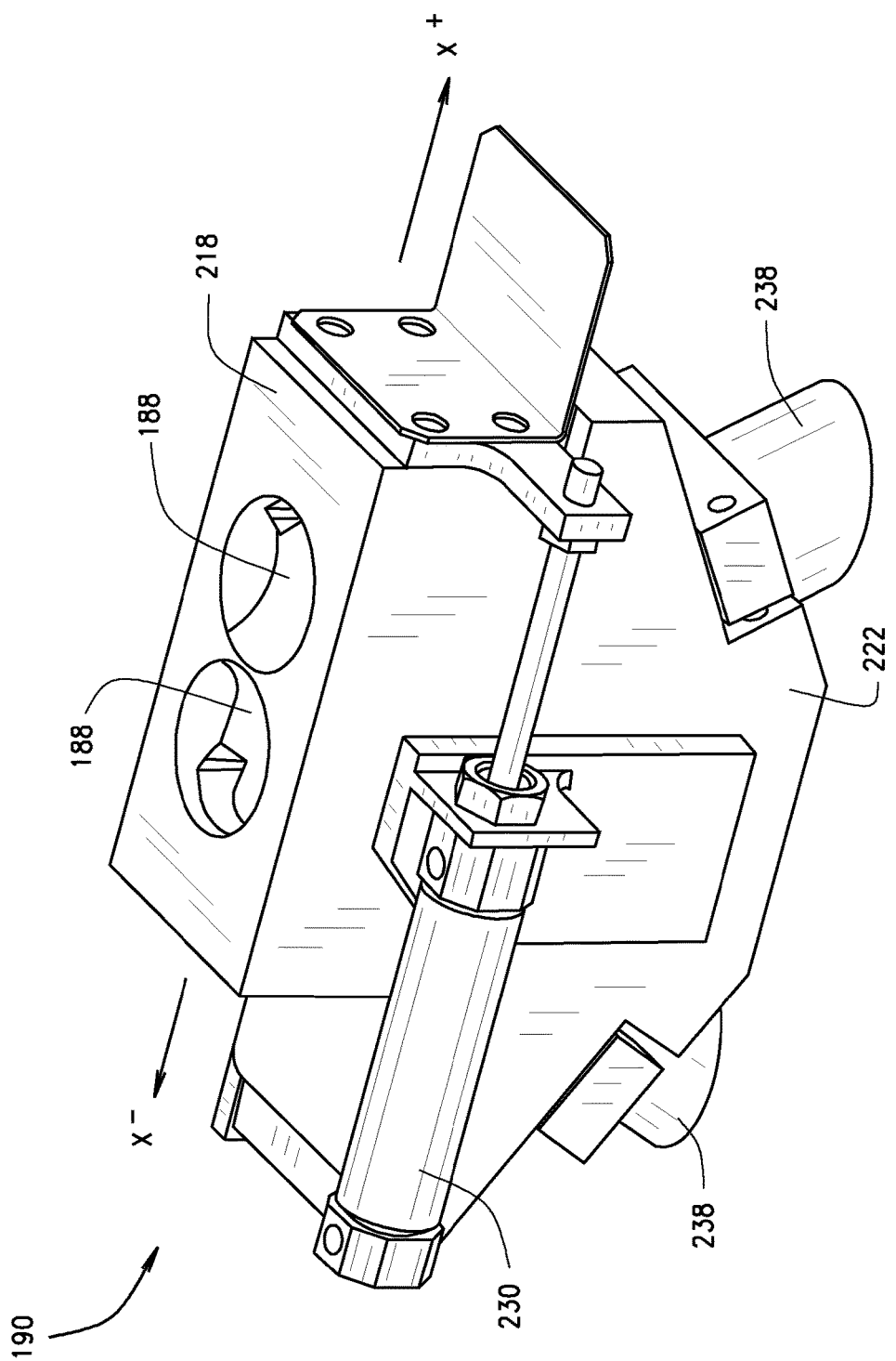
FIG. 10 is an isometric view of a diverter unit included in the diverter and accumulator module shown in FIG. 9, in accordance with various embodiments of the present disclosure.
Figure 11:
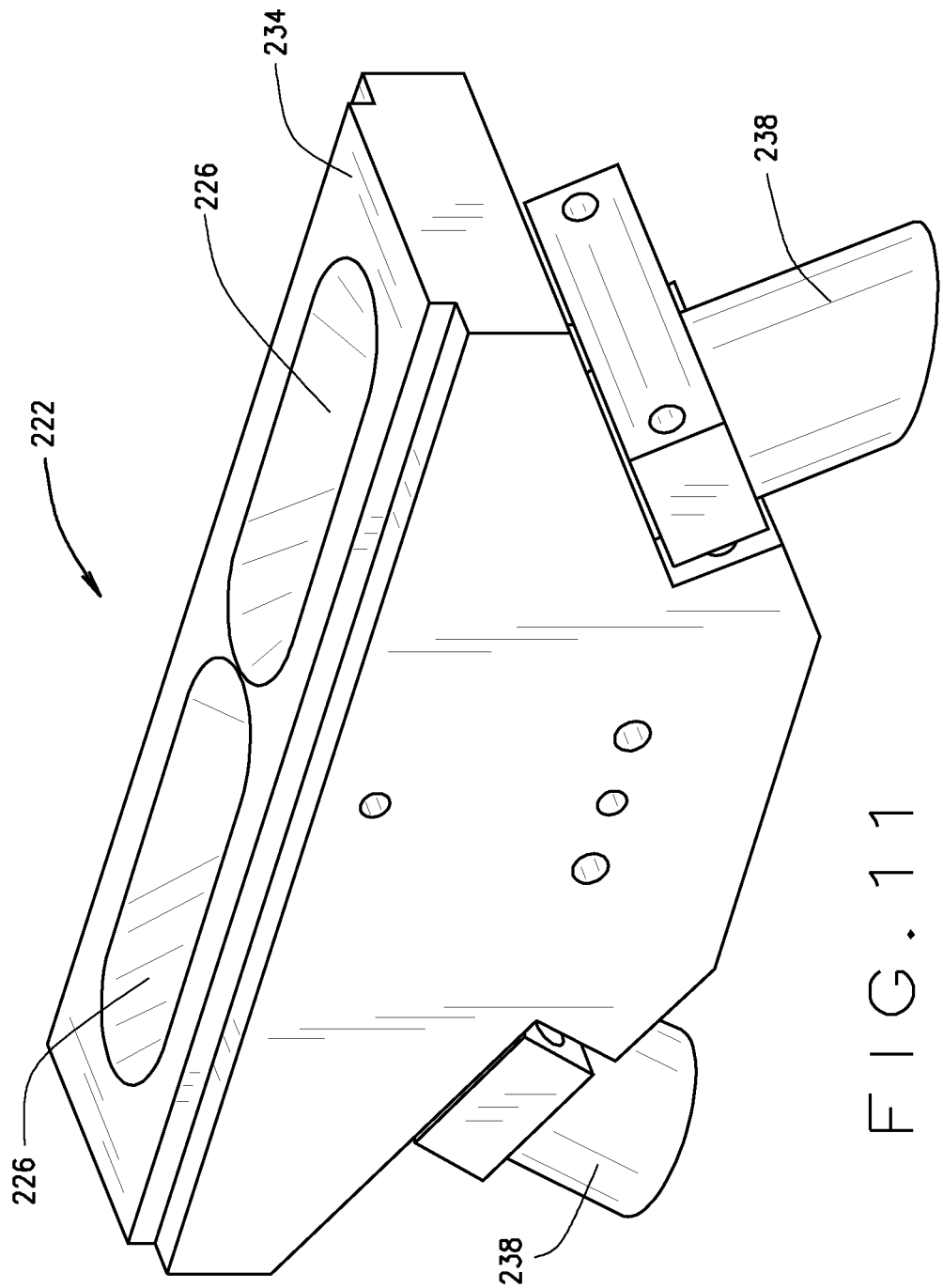
FIG. 11 is an isometric view of a base of the diverter unit shown in FIG. 10, in accordance with various embodiments of the present disclosure.

Referring now to FIG. 9, in various embodiments, in addition to the diverter unit 190, the D&A module 26 includes an accumulator unit 214 mounted to system support structure beneath the diverter unit 190. Generally, the diverter unit 190 receives singulated objects from the O&C device 50, via the diverting channels 188, parses the objects into the various programmed groups, and directs each group to one of the discharge funnels 34. In turn, the accumulator unit 214 receives the each group of objects and, via the discharge funnels 34, directs each respective group to the respective corresponding object collection receptacle 14.

Referring now to FIGS. 9, 10, 11, 12 and 13, in various embodiments, the diverter unit 190 includes a diverter head 218 slidingly engaged with a diverter base 222. The diverter head 218 includes the plurality of diverting channels 188 that extend through the diverter head 218 in different directions. Each diverting channel 188 includes an upper end 224 and an opposing lower end 225. The diverter base 222 includes a plurality of diverting funnels 226 extending through the diverter base 222. The diverter unit 190 additionally includes a linear actuator 230 that is operable, via control by the master control system 18, to bidirectionally move the diverter head 218 longitudinally along a top 234 of the diverter base 222 in the X+ and the X− directions. More particularly, the diverter head 218 is movable, via the linear actuator 230, between a plurality of diverting positions. In each of the diverting positions, the upper end 224 of a different one of the diverting channels 188 aligns with the bottom portion 170 of the O&C device tubular body 162. Additionally, when the upper end 224 of a particular diverting channel 188 aligns with the tubular body bottom portion 170, the lower end 225 of the particular diverting channel 188 is positioned to simultaneously align with a corresponding one of the diverting funnels 226 in the diverter base 222. Accordingly, each respective group of objects can be selectively diverted, i.e., directed or routed, from the tubular body bottom portion 170 to a particular one of the diverting funnels 226 by controllably moving the diverter head 218 along the top 234 of the diverter base 222.

The diverter unit 190 further includes a plurality of diverting tubes 238 coupled to diverter base 222. The diverting tubes 238 are coupled to the diverter base 222 such that each diverting tube 238 extends from a distal end 242 of a corresponding one of the diverting funnels 226 and terminates above a corresponding one of the accumulator unit discharge funnels 34. Therefore, by selectively routing each group of objects to a particular diverting funnel 226, as described above, the objects are consequently selectively directed to a particular corresponding discharge funnel 34 of the accumulator unit 214, via the diverting tubes 238.

For example, in various embodiments, the diverter head 218 can include a pair of diverting channels 188 that angularly extend through the diverter head 218 in opposing directions with respect to a longitudinal axis of the diverter head 218. Similarly, the diverter base 222 can include a pair of the diverting funnels 226 and respective diverting tubes 238, and the accumulator unit 214 can correspondingly include a pair of discharge funnels 34. In such embodiments, the actuator 230 can be controlled to position the diverter head 218 between a first routing position (shown in FIG. 12) and second routing position (shown in FIG. 13). In the first routing position (shown in FIG. 12) a first one of the diverting channels 188 is aligned with the O&C device tubular body bottom portion 170 and a corresponding first one of the diverting funnels 226. Therefore, as singulated objects pass the counting device 174, a first programmed group of objects are counted and deposited into the first diverting channel 188. Consequently, the first group of objects travel through the first diverting channel 188 and are deposited into a first one of the discharge funnels 34. The first group of objects then travel through the first discharge funnel 34 and are deposited into the proper corresponding first collection receptacle 14.

Once the counting device 174 and master control system 18 determine that the first programmed number of objects, i.e., the first programmed group of objects, have passed the counting device 174, the master control system 18 moves the diverter head 218 to the second routing position (shown in FIG. 13) without interrupting operation of the S&C module 22, i.e., without interrupting the flow of objects traveling through the O&C device 50. In the second routing position, a second one of the diverting channels 188 is aligned with the O&C device tubular body bottom portion 170 and a corresponding second one of the diverting funnels 226. Therefore, as singulated objects continue to pass the counting device 174, a second programmed group of objects are counted and deposited into the second diverting channel 188. Consequently, the second group objects travel through the second diverting channel 188 and are deposited into a second one of the discharge funnels 34. The second group of objects then travel through the second discharge funnel 34 and are deposited into the proper corresponding second collection receptacle 14.

Once the counting device 174 and master control system 18 determine that the second programmed number of objects, i.e., the second programmed group of objects, have passed the counting device 174, the master control system 18 moves the diverter head 218 to the first routing position (shown in FIG. 12) without interrupting operation of the S&C module 22, i.e., without interrupting the flow of objects traveling through the O&C device 50. Furthermore, as described further below, substantially simultaneously, the master control system 18 will control the operation of the OC module 30 to position a subsequent pair of collection receptacles 14 beneath the respective first and second discharge funnels 34. Thereafter, a third and fourth group of objects are parsed from the substantially continuous flow of singulated objects traveling through the O&C device 50 and deposited into the corresponding third and fourth collection receptacles 14. This process will continue until each of the plurality of collection receptacles 14 have received the respective corresponding programmed group of objects.

It should be understood that although the various figures exemplarily illustrate a pair of diverting channels 188, a pair of the diverting funnels 226 and a pair of discharge funnels 34, the present disclosure should not be so limited. In various other embodiments, as should be readily understood by one skilled in the art based on the present disclosure, the D&A module 26 can include more than a pair, e.g., three or more, of the diverting channels 188, the diverting funnels 226 and the discharge funnels 34.

Referring now to FIGS. 9, 12, 13, 14 and 15, in various embodiments, the accumulator unit 214 includes a sluice plate 246 slidingly engaged with an accumulator base 250 that includes the plurality of discharge funnels 34 extending through the accumulator base 250. The accumulator unit 214 additionally includes a linear actuator 254 that is operable, via control by the master control system 18, to bidirectionally move the sluice plate 246 longitudinally along a top 258 of the accumulator base 250 in the X+ and the X– directions. More particularly, the sluice plate 246 is movable, via the linear actuator 254, between an object dispensing position (shown in FIG. 12) and an object accumulating position (shown in FIG. 13). When in the object dispensing position, each of a plurality of apertures 262 in the sluice plate 246 align with a corresponding one of the diverting tubes 238. Thus, when in the object dispensing position, objects diverted to the diverting funnels 226, as described above, will pass through the diverting tubes 238 and the corresponding sluice plate apertures 262 into the corresponding discharge funnels 34.

However, when in the object accumulating position, the sluice plate apertures 262 are not aligned with the diverter tubes 238, rather a solid portion 266 of the sluice plate 246, i.e., the portion of the sluice plate 246 not including the apertures 262, will cover, or block, a discharge end 270 of the diverting tubes 238. Thus, when in the object accumulation position, objects are blocked by the sluice plate solid portion 266 and prevented from passing from the diverting tubes 238 into the corresponding discharge funnels 34. Therefore, objects will accumulate within the diverting tubes 238 until the master control system 18 moves the sluice plate 246 to the object discharge position, via the actuator 254.

In various embodiments, the sluice plate 246 will be placed in the object accumulating position as the OC module 30 moves filled collection receptacles 14, i.e., collection receptacles 14 that have received the respective corresponding programmed group of objects, from beneath the discharge funnels 34 and moves the next set of empty collection receptacles 14 beneath the discharge funnels 34, as described further below. Therefore, once a set of collection receptacles 14 have received the respective corresponding group of objects, the master control system 18 will move the sluice plate 246 to the object accumulating position, via the actuator 254, allowing the S&C module 22 and diverter unit 190 to continue to operate without interruption. The objects will then accumulate in at least one of the diverting tubes 238 while the filled collection receptacles 14 are automatically replaced with the next set of empty collection receptacles 14. Once the next set of empty collection receptacles 14 are positioned at a target location beneath the discharge funnels 34, the master control system 18 will move the sluice plate 246 to the object dispensing position, via the actuator 254, thereby allowing the respective corresponding groups of objects, comprised of the accumulated objects and/or subsequently singulated objects, to be deposited into the empty collection receptacles 14.

In various embodiments, the master control system 18 can stop or pause operation of the small object counting system 10 when the count of objects accumulated in any of the diverting tubes 238 reaches a maximum threshold amount and/or the next set of empty collection receptacles 14 are not positioned at the target location beneath the discharge funnels 34 within a maximum threshold time.

The diverter unit and accumulator unit linear actuators 230 and 254 can be any linear actuator controllable by the master control system 18 and suitable to bidirectionally move the respective diverter head 218 and sluice plate 246 in the X+ and the X– directions. For example, in various embodiments, the diverter unit and accumulator unit linear actuators 230 and 254 can be pneumatically operated linear actuators. Alternatively, in various embodiments, the diverter unit and accumulator unit linear actuators 230 and 254 can be electrically or hydraulically operated linear actuators.

Referring now to FIGS. 1, 16, 17 and 18, in various embodiments, the collection module 30 includes one or more collection receptacle racks 274 removably mounted on a linear stage 278. The collection receptacle rack(s) is/are structured to retain a plurality of sets 14A of collection receptacles 14. Although, in various embodiments, the collection module 30 can includes a plurality of collection receptacle racks 274 removably mounted on a linear stage 278, for simplicity and clarity, only a single collection receptacle rack 274 is illustrated and described. Additionally, it should be understood that although the various figures exemplarily illustrate the collection receptacle rack 274 being structured to retain a plurality of collection receptacle sets 14A that each comprise a pair of collection receptacles 14, the present disclosure should not be so limited. In various other embodiments, as should be readily understood by one skilled in the art based on the present disclosure, that the collection receptacle rack 274 can be structured to retain a plurality of collection receptacle sets 14A that each comprises more than a pair, e.g., three or more, of the collection receptacles 14. Furthermore, although the various figures exemplarily illustrate the collection receptacles 14 as being envelopes, it should be understood that the collection receptacle rack 274 can be structured to retain any suitable collection receptacles 14. For example, in various embodiments, the collection receptacle rack 274 can be structured to retain other types of collection receptacles 14 such as beakers, cans, cups, jars, bags, trays, etc.

The linear stage 278 is controllable by the master control system 18 to sequentially position each of the sets 14A of collection receptacles 14 beneath the accumulator object discharge funnels 34. More particularly, the linear stage 278 includes a translating track 282 and an actuator 286 operable to bidirectionally move a carriage 290 along the length of the translating track 282. The collection receptacle rack 274 is structured to be removably retained on the carriage 290. Thus, the actuator 286 is controlled by the master control system 18 to sequentially position each set 14A of collection receptacles 14 at the target location beneath the accumulator base 250, wherein a discharge end 294 of each discharge funnel 34 (shown in FIGS. 12 and 13) is directly above a respective collection receptacle 14 of the set 14A. Therefore, each programmed group of objects parsed from the flow of singulated objects will be deposited into the respective corresponding collection receptacle 14.

As described above, in various embodiments, the D&A module 26 includes the sluice plate 246 that can be placed in the object accumulating position (shown in FIG. 13) as the OC module 30 moves filled collection receptacles 14 from the target location and moves the next set 14A of empty collection receptacles 14 to the target position. Therefore, once each set 14A of collection receptacles 14 has received the respective corresponding groups of objects, the master control system 18 will move the sluice plate 246 to the object accumulating position, via the actuator 254, such that the objects are prevented from exiting the diverting tubes 238. Substantially simultaneously, the master controller 18 will move the carriage 290, via the actuator 286, along the track 282 to position the next set 14A of collection receptacles 14 at the target location. Once the next set 14A of collection receptacles 14 is positioned at the target location, the master control system 18 will move the sluice plate 246 to the object dispensing position to allow the subsequent parsed groups of objects to be deposited into the respective collection receptacle 14.

The linear stage actuator 286 can be any linear actuator controllable by the master control system 18 and suitable to bidirectionally move the carriage 290 and respective collection receptacle rack 274 along the linear stage track 282. For example, in various embodiments, the linear stage actuator 286 can be a pneumatically operated linear actuator. Alternatively, in various embodiments, the linear stage actuator 286 can be an electrically or hydraulically operated linear actuator.

In various embodiments, the collection receptacle rack 274 can include a top plate 298 having a plurality of tubular receptacle spouts 302 extending from a plurality of apertures 306 in the top plate 298. Each spout 302 is structured to removably retain a top portion of a respective one of the object collection receptacles 14. Additionally, the apertures 306 comprise a plurality of sets 306A of apertures 306, wherein the respective spouts 302 extending from each set 306A of apertures 306 removably retain a respective set 14A of the collection receptacles 14. Moreover, the sets 306A of apertures 306 are located within the top plate 298 such that each respective set 306A of apertures 306 will be positioned at the target location as the master controller 18 sequentially moves the carriage 290 along the track 282 to deposit each programmed group of objects into the respective corresponding collection receptacle 14, as described above. Therefore, in such embodiments, as each group of parsed objects exits the discharge end 294 of the corresponding discharge funnel 34, each group of objects will travel through the respective aperture 306 and spout 302, thereby directing each group of objects into the respective collection receptacle 14.

Additionally, in various embodiments, the collection receptacle rack 274 includes a bottom plate 310 that includes a plurality of recessed bays 314. Each recessed bay 314 is structured to support and removably retain a bottom portion of a respective one of the object collection receptacles 14. Therefore, each collection receptacle will remain properly oriented during operation of the OC module 30.

Figure 17:
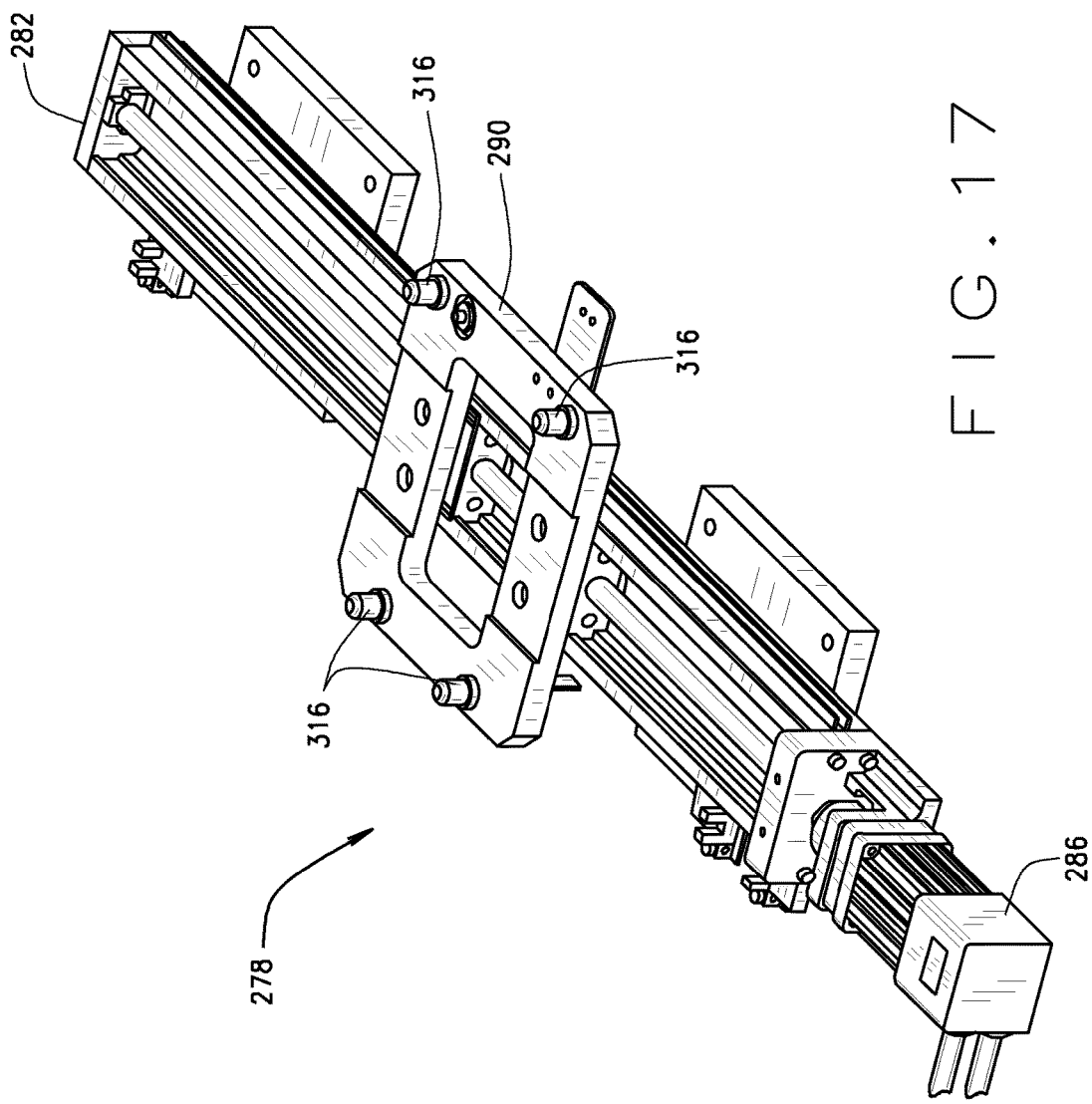
FIG. 17 is an isometric view of a linear stage of the collection module shown in FIG. 16, in accordance with various embodiments of the present disclosure.
Figure 18:
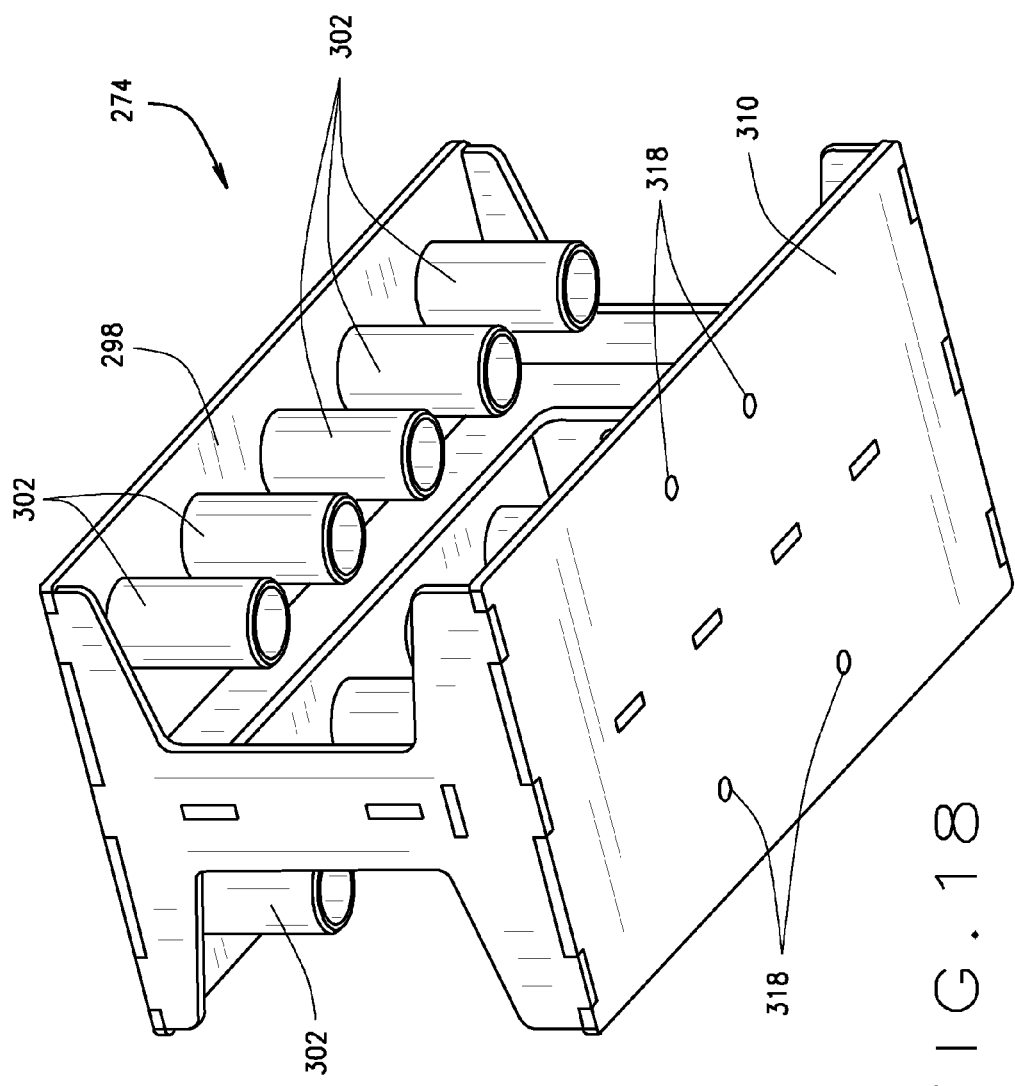
FIG. 18 is an isometric view of collection receptacle rack of the collection module shown in FIG. 16, in accordance with various embodiments of the present disclosure.

With particular reference to FIGS. 17 and 18, in various embodiments, the collection receptacle rack mounting carriage 290 includes a plurality of locating pins 316. The locating pins 316 are structured to removably mate with a plurality of locating pin receivers 318 included in the bottom plate 310 of the collection receptacle rack 274. Accordingly, to removably mount the collection receptacle rack 274 on the carriage 290, each locating pin receiver 318 is mated with a respective one of the locating pins 316. Additionally, the locating pins 316 and locating pin receivers 318 are respectively arranged on the carriage 290 and within the bottom plate 310 in a particular pattern such that when mated together the collection receptacle rack 274 will be precisely mounted on the carriage 290 in a particular location and orientation. That is, when the locating pin receivers 318 are mated with the locating pins 316, the collection receptacle rack 274 will be removably retained on the 290 carriage in a substantially precise location and orientation. Therefore, the linear stage 278 can be controlled to sequentially position each of the collection receptacles 14, or in various embodiments, the top plate apertures 306, directly under the discharge end 294 of a respective one of the discharge funnels 34 to deposit each group of singulated objects in the respective corresponding one of the object collection receptacles 14.

Figure 19:
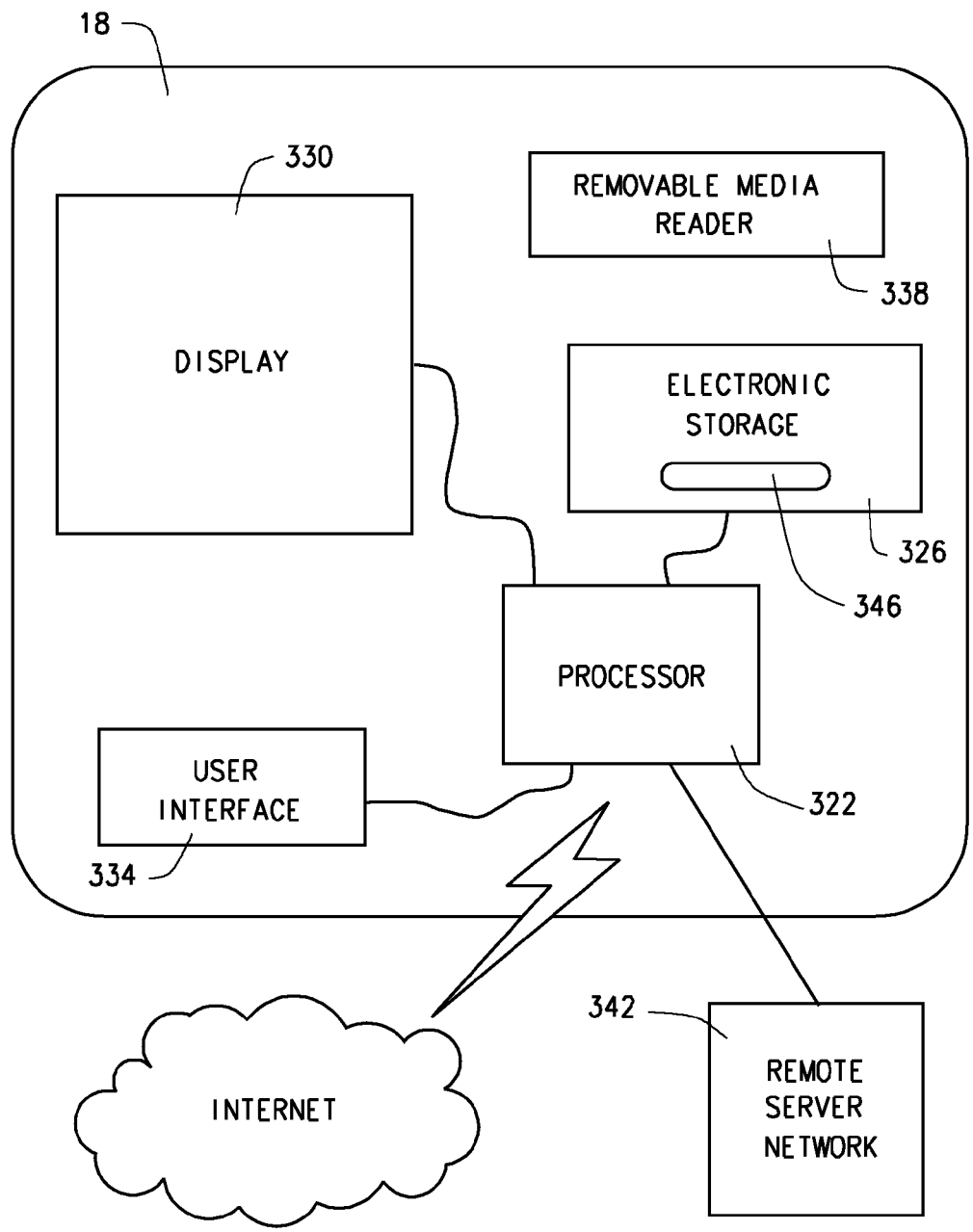
FIG. 19 is a block diagram of a master control system of the small object counting system shown in FIG. 1, in accordance with various embodiments of the present disclosure.

Referring to FIG. 19, in various embodiments, the master control system 18 is a computer based system that generally includes at least one processor 322 suitable to execute all functions of the master control system 18 to automatically, or robotically, control the operation of the small object counting system 10, as described herein. The master control system 18 can additionally include at least one electronic storage device 326 that comprises a computer readable medium, such as a hard drive or any other electronic data storage device for storing such things as software packages or programs, algorithms and digital information, data, look-up tables, electronic spreadsheets and databases. Furthermore, the master control system 18 can include a display 330 for displaying such things as information, data and/or graphical representations, and at least one user interface device 334, such as a keyboard, mouse, stylus, scanner and/or an interactive touch-screen on the display 330. In various embodiments the master control system 18 can further include a removable media reader 338 for reading information and data from, and/or writing information and data to, removable electronic storage media such as floppy disks, compact disks, DVD disks, zip disks, or any other computer readable removable and portable electronic storage media. In various embodiments, the removable media reader 338 can be an I/O port of the master control system 18 utilized to read external or peripheral memory devices such as thumb drives, memory sticks/cards or external hard drives.

In various embodiments, the master control system 18 is communicatively connectable to a remote server network 342, e.g., a local area network (LAN), via a wired or wireless link. Accordingly, the master control system 18 can communicate with the remote server network 342 to upload and/or download data, information, algorithms, software programs, etc., and/or receive operational commands from the remote server network 342. Additionally, in various embodiments, the master control system 18 is configured to access the Internet to upload and/or download data, information, algorithms, software programs, etc., to and from Internet sites and network servers.

Additionally, in various embodiments, the master control system 18 includes a small object counting program 346, stored on the storage device 326 and executed by processor 322 using inputs from the user interface 334 and various components, sensors, systems and assemblies of the small object counting system 10. Particularly, the small object counting program 346 can include various routines and subroutines that control all operations of the small object counting system 10 described herein.

Figure 16:
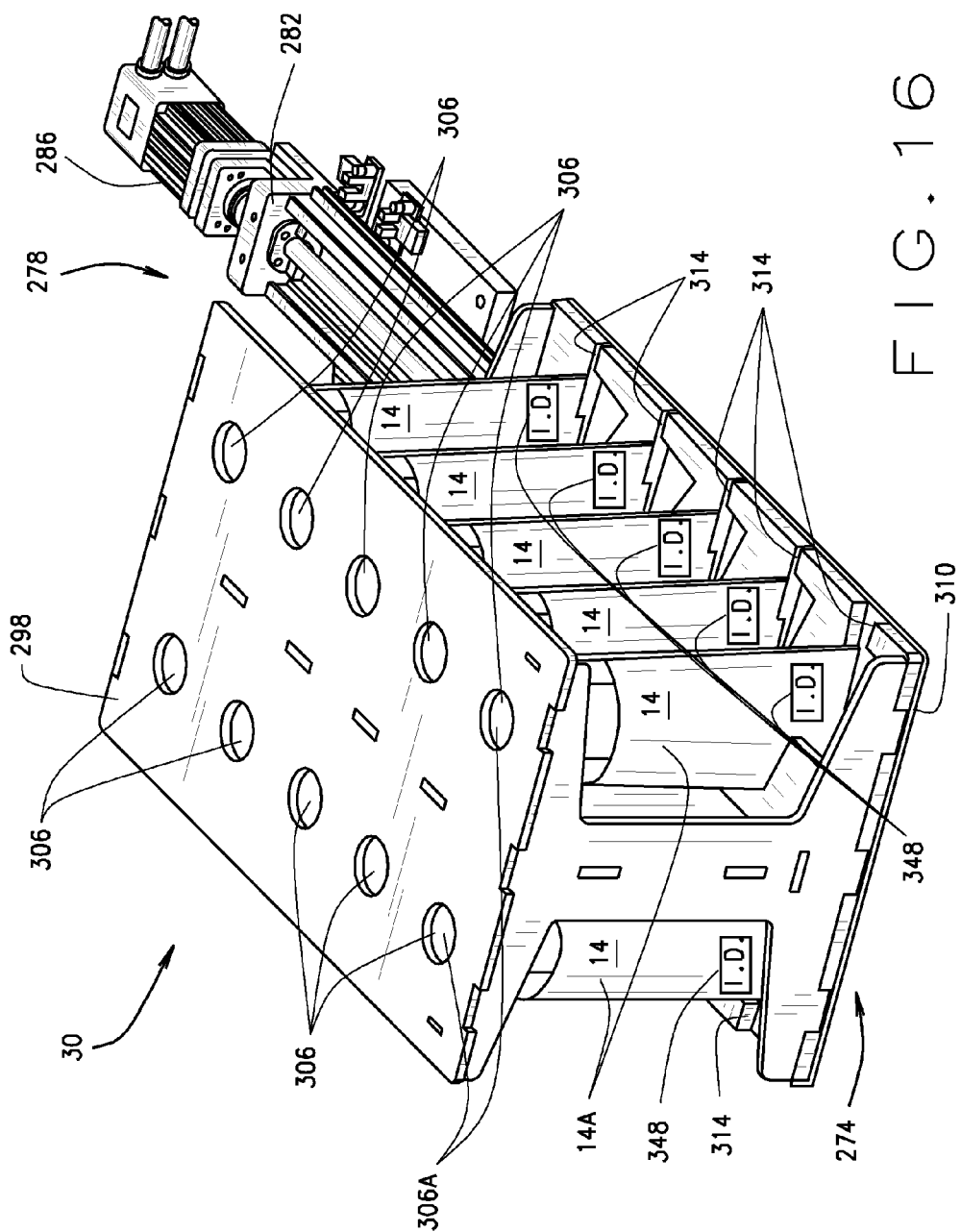
FIG. 16 is an isometric view of a collection module included in the small object counting system shown in FIG. 1, in accordance with various embodiments of the present disclosure.

Referring now to FIG. 16, in various embodiments, each collection receptacle 14 includes an information device 348 attached thereto. Each collection receptacle information device 348 provides various information, i.e., data, regarding the objects to be deposited into the respective collection receptacle 14, that is compiled and stored for access by the master control system 18 to control the number of objects to be deposited into each respective corresponding collection receptacle 14, as described above. For example, in various embodiments, each information device 348 can provide data regarding the particular type and number of objects to be deposited into the respective collection receptacle 14. Additionally, each information device 348 can provide data regarding the specific genotypes or attributes of the particular objects to be deposited in each respective collection receptacle 14, e.g., characteristics and/or traits such as size, shape, color, composition, quality, weight, genetic traits, etc. The data provided by each identification device 348 can be compiled and stored for access by the master control system 18 in any suitable or desirable format.

For example, the data can be compiled and stored locally, e.g., stored on the electronic storage device 326, as one or more electronic databases, spreadsheets and/or look-up tables. Therefore, during execution of the small object counting program 346 by the master control system processor 322, the data can be directly accessed and utilized to control operation of the small object counting system 10, as described above. In other embodiments, the data can be stored remotely, e.g., on the remote server network 342 or a secure Internet site, as one or more electronic databases, spreadsheets and/or look-up tables. Therefore, during execution of the small object counting program 346 the data must be accessed from the remote location or site to control operation of the small object counting system 10. In yet other embodiments, the data can be stored, as one or more electronic databases, spreadsheets and/or look-up tables, on a removable electronic storage media, e.g., floppy disks, compact disks, DVD disks, zip disks, thumb drives, or any other computer readable removable and portable electronic storage media. Therefore, during execution of the small object counting program 346 the data must be accessed from the removable electronic storage media to control operation of the small object counting system 10, as described herein.

In various embodiments, each collection receptacle information device 348 can be automatically 'read', or interpreted, by the user interface 334 and automatically input and stored on the electronic storage device 326 or other computer readable media accessible by the master control system 18 during execution of the small object counting program 346. For example, in various embodiments, each information device 348 comprises a 'bar code' label and the user interface 334 comprises any suitable bar code reader, e.g., a hand held bar code reader. Thus, prior to operation of the small object counting system 10, i.e., prior to the singulating, counting, parsing of the objects, a user or operator scans the bar code information device 348 of each collection receptacle 14 and then places each collection receptacle 14 in the rack 274. The read information is subsequently stored on the electronic storage device 326 or other computer readable media in a desired format, e.g., an electronic spreadsheet. During execution of the small object counting program 346 the processor 322 accesses and interprets the stored information and controls the operation of the small object counting system 10 to singulate, count, parse and deposit the particular number of objects in each respective collection receptacle 14, as articulated by the stored information.

In various other embodiments, each collection receptacle information device 348 can comprise any other sort of 'readable' label and the user interface 334 can comprise any suitable corresponding automated label reader. For example, the each information device 348 can comprise a magnetic tag or a magnetic strip readable by a suitable magnetic tag or strip reader user interface 334. Alternatively, each information device 348 can comprise an electronic tag or device readable by a suitable electronic tag or device reader user interface 334. In still other embodiments, each information device 348 can comprise any other sort of human readable or interpretable label. In which case, the user or operator would read each information device 348 and manually input the data directly into the master control system 18 using the user interface 334, e.g., a keyboard, mouse, stylus or touch-screen display.

Figure 20:
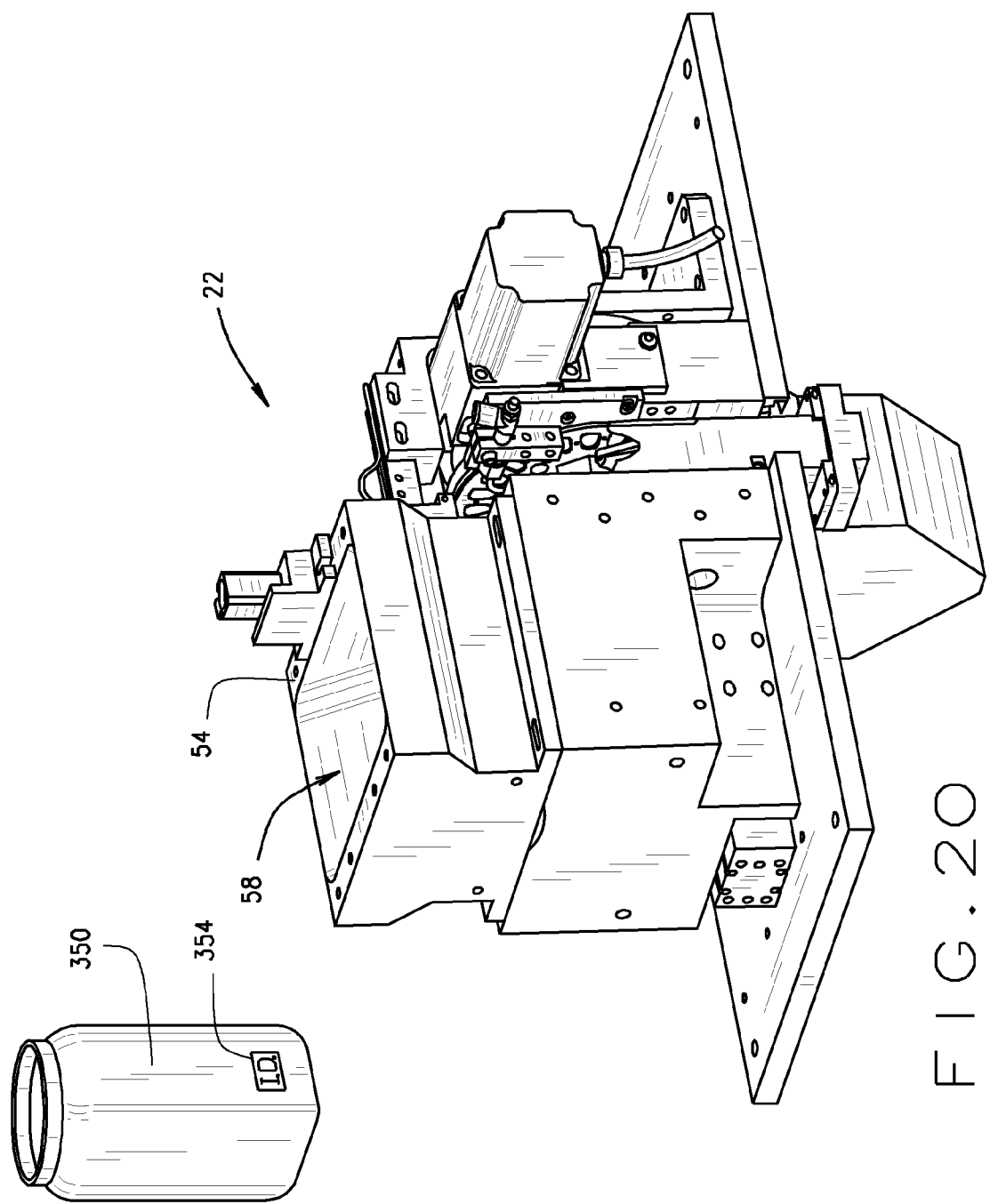
FIG. 20 is an isometric view of the singulating and counting module included in the small object counting system shown in FIG. 1, illustrating a bulk object container for providing objects to the singulating and counting module, in accordance with various embodiments of the present disclosure.

Referring now to FIG. 20, in various embodiments, the large volume of objects to be singulated, counted, parsed and deposited into the plurality of collection receptacles 14 can be stored in a bulk object source container 350 structured to retain the large volume of objects or more. Moreover, a plurality of different types of objects can be stored in a plurality of source containers 350. Accordingly, to singulate, count, parse and deposit a large quantity of a particular type of objects, as describe above, the large volume of the particular objects are removed from the respective source container 350 and deposited into the bulk object hopper 38. In various implementations, each source container 350 includes a source container identification device 354 attached thereto. Each source container identification device 354 provides various information, i.e., data, regarding the objects retained within the respective bulk object container 350. For example, in various embodiments, each source container identification device 354 can provide data regarding the particular genotypes or attributes of the particular objects retained within the respective source container 350, e.g., characteristics and/or traits such as size, shape, color, composition, quality, weight, genetic traits, etc.

Similar to the collection receptacle information devices 348, source container identification device 354 can be automatically 'read', or interpreted, by the user interface 334 and automatically input and stored on the electronic storage device 326 or other computer readable media accessible by the master control system 18 during execution of the small object counting program 346.

For example, in various embodiments, each source container identification device 354 can comprise a 'bar code' label and the user interface 334 can comprise any suitable bar code reader, e.g., a hand held bar code reader. Prior to operation of the small object counting system 10, i.e., prior to execution of the small object counting program 346, a user or operator scans the bar code source container identification device 354 of the respective bulk object source container 350 from which the large quantity of objects were, or will be, removed and deposited into the bulk object hopper 54. The read source container identification data is subsequently stored on the electronic storage device 326 or other computer readable media, as described above. During execution of the small object counting program 346, the stored source container identification data is accessed and compared with the portion of the information read from each of the collection receptacle information devices 348 that stipulates the type of objects to be deposited into each respective collection receptacle 14.

Based on the comparison, execution of the small object counting program 346 will be continued, paused or ceased. That is, if the comparison determines that the respective source container 350 is for storing the proper objects to be deposited into the collection receptacles 14, execution of the small object counting program 346 will continue. Alternatively, if the comparison determines that the respective source container 350 is for storing a different type of objects than that articulated by the respective collection receptacle information devices 348, execution of the small object counting program 346 can be paused until the proper bulk object container 350 is identified. Or, in such instances, execution of the small object counting program 346 can be terminated.

In various other embodiments, each source container identification device 354 can comprise any other sort of 'readable' label and the user interface 334 can comprise any suitable corresponding automated label reader. For example, the each source container identification device 354 can comprise a magnetic tag or a magnetic strip readable by a suitable magnetic tag or strip reader user interface 334. Alternatively, each source container identification device 354 can comprise an electronic tag or device readable by a suitable electronic tag or device reader user interface 334. In still other embodiments, each source container identification device 354 can comprise any other sort of human readable or interpretable label. In which case, the user or operator would read each source container identification device 354 and manually input the data directly into the master control system 18 using the user interface 334, e.g., a keyboard, mouse, stylus or touch-screen display.

Referring generally to FIG. 19, in various embodiments, during operation of the small object counting system 10, execution of the small object counting program 346, can track and store 'actual' counts of objects deposited into each respective collection receptacle 14. That is, if more than or fewer than the programmed number of objects is actually deposited into a particular collection receptacle 14, the 'actual' count will indicate the overage or underage. For example, in various implementations, the programmed amounts can be stored in an electronic spreadsheet, as described above. In such implementations, the 'actual' count can be likewise entered and stored in the electronic spreadsheet, which can then be printed out and/or stored for future reference. Additionally, in various embodiments, execution of the small object counting program 346, can enter and store other information for future reference, such as time and date of the deposit of the objects into each respective collection receptacle 14, or any other desired information.

Still further, in various embodiments, execution of the small object counting program 346, can allow operation of the small object counting system to be paused, and then resumed during completion of a particular 'run'. For example, in implementations wherein the information read from the collection receptacle information devices 348 is stored in an electronic spreadsheet, operation of the small object counting system 10 can be paused at any point on the spreadsheet, and then subsequently be resumed at the same point on the spreadsheet. That is, operation of the small object counting system 10 can be paused at any point of completion of the process of depositing the objects into the collection receptacles 14 as stipulated by the spreadsheet and subsequently resumed at the same point of completion without reprogramming the spreadsheet, i.e., without entering new data into the spreadsheet. For example, in instances where a particular electronic spreadsheet comprises information pertaining to a plurality of collection receptacles 14 retained in a plurality of collection receptacle racks 274, the system 10 can be paused to remove a rack of collection receptacles 14 that have received the respective number of objects stipulated by the spreadsheet. Subsequently, a rack of empty collection receptacles 14 can be mounted on the linear stage 278 (shown in FIG. 17), and the process resumed to deposit the respective number of objects into the subsequent collection receptacles 14 as stipulated by the spreadsheet.

Figure 21:
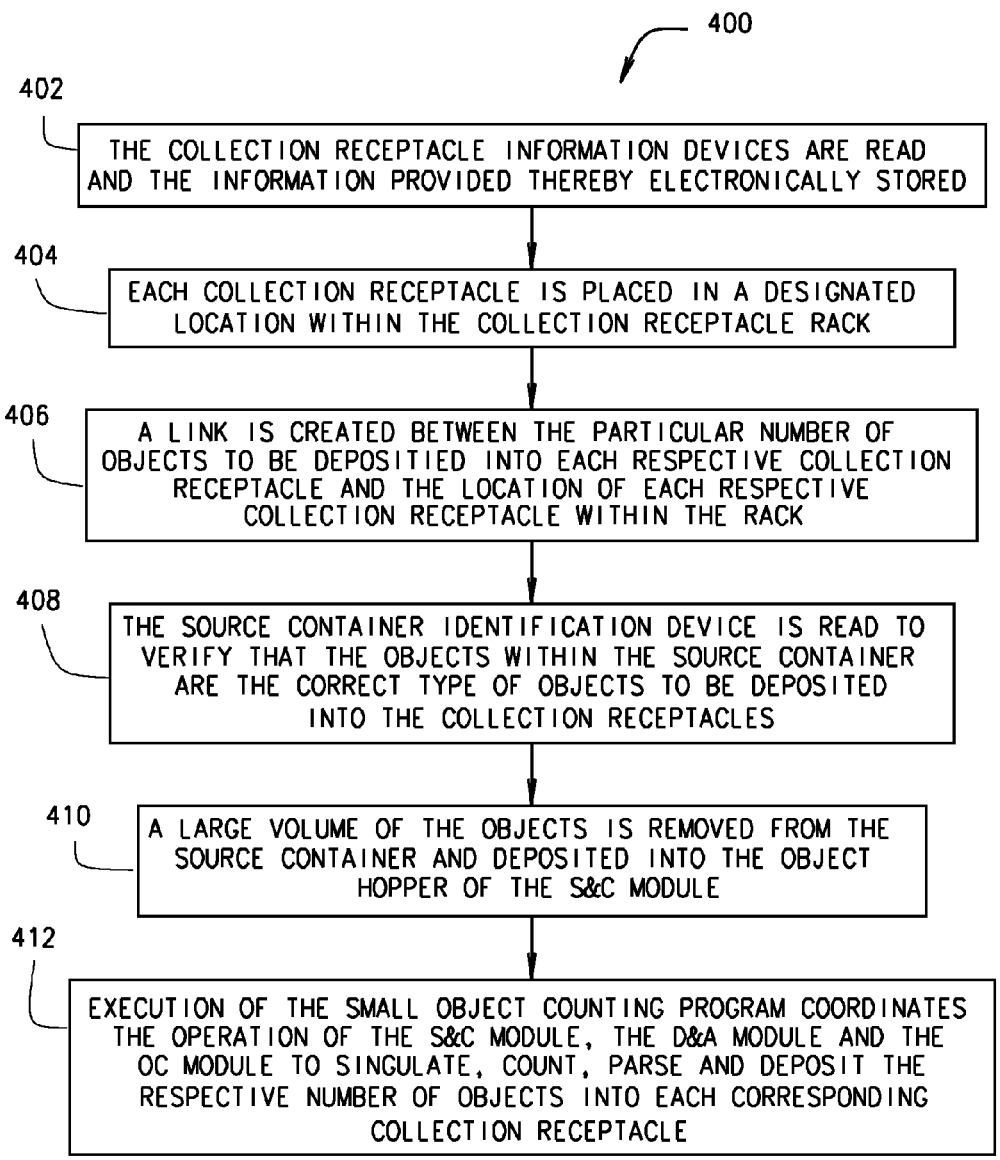
FIG. 21 is a flow chart illustrating the operation of the small object counting system shown throughout FIGS. 1 though 20, in accordance with various embodiments of the present disclosure.

FIG. 21 provides a flow chart 400 illustrating the operation of the small object counting system 10, in accordance with various embodiments. Initially, the collection receptacle information device 348 of each of the plurality of collections receptacles 14 is read and the information provided thereby is electronically stored, as indicated at 402. As described above, the information provided by each respective collection receptacle information device 348 can be stored in an electronic spreadsheet or any other suitable format that is accessible and interpretable during execution of the small object counting program 346.

In various embodiments, the small object counting program 346 can include a collection receptacle loading subroutine that requests the information from each collection receptacle information device 348 be read. i.e., input, and identifies a location within a respective collection receptacle rack 274 in which each respective collection receptacle 14 is to be placed. Therefore, as each respective information device 348 is read, the respective collection receptacle 14 is placed in a particular location within the rack 274 as directed by the collection receptacle loading sub-routine, as indicated at 404. Accordingly, a link is created between the particular number of objects to be deposited into each respective collection receptacle 14 and the location of each respective collection receptacle within the rack 274, as indicated at 406. Therefore, via execution of the small object counting program 346, the master control system 18 can control and coordinate the operation of the D&A module 26 with the operation of the OC module 30, i.e., the operation of the linear stage 278, to deposit the correct number of objects into each respective collection receptacle 14.

The source container identification device 354 is then read and compared to information provided by the collection receptacle information devices 348 to verify that the objects within the source container 350 are the correct type of objects to be deposited into the collection receptacles 14, as indicated at 408. Once the objects within the source container 350 have been verified to by the proper objects, a large volume of the objects is removed from the source container 350 and deposited into the object hopper 54 of the S&C module 22, as indicated at 410. Thereafter, as indicated at 412, execution of the small object counting program 346 will coordinate the operation of the S&C module 22, the D&A module 26 and the OC module 30 to singulate, count, parse and deposit the respective groups of objects into each corresponding collection receptacle 14, based on the information read from each respective information device 348, as described above.

Thus, the small object counting system 10 can automatically deposit a different number objects into each respective collection receptacle 14, as articulated by the data stored in the electronic spreadsheet, or any other form of database. That is, via execution of the small object counting program 346, and based on the data stored in the spreadsheet, or any other form of database, the master control system 10 sequentially moves each respective collection receptacle 14 to the target location and automatically controls the number of objects deposited into each collection receptacle 14, which can vary from one collection receptacle 14 to the next. More particularly, via execution of the small object counting program 346 and the stored data, the master control system 10 can dynamically modify the number of objects being parsed by the D&A module 26 to deposit a different number of objects in each respective collection receptacle 14.

The small object counting system 10, as described herein, is structured and operable singulate, count, parse and deposit the respective number of objects into each corresponding collection receptacle 14 with a high rate of accuracy and speed. For example, in various embodiments, the small object counting system 10 can accurately singulate and count the object at a rate of approximately 15 to 25 objects a second. The time to parse and deposit each respective group of objects into the corresponding collection receptacles 14 will vary depending on the number of objects stipulated to be in each respective group. Additionally, the time to parse and deposit each respective group of objects into the corresponding collection receptacles 14 can vary with regard to the difference in the number of objects to be deposited into the respective different collection receptacles 14 within a particular collection receptacle rack 274.

It should be understood that, although the terms first, second, third, etc. have been used herein to describe various elements, components, sections, regions, etc., these elements, components, sections, regions, etc., should not be misconstrued to indicate priority or importance elements, components, sections, regions, etc. These terms have been used merely to distinguish one element, component, section, region, etc., from another element, component, section, region, etc.

The description herein is merely exemplary in nature and, thus, variations that do not depart from the gist of that which is described are intended to be within the scope of the teachings. Such variations are not to be regarded as a departure from the spirit and scope of the teachings.

What is claimed is:

1. A system for counting small objects, said system comprising:
   a singulating and counting assembly structured and operable to singulate a plurality of objects from a large volume of the objects and count the singulated objects;
   a diverter assembly structured and operable to receive the singulated objects, parse the received objects into a plurality of groups of objects, at least one of the groups of objects comprising a different number of objects than at least one other group of objects, and direct each group of objects into a selected one of a plurality of diverting tubes of the diverter unit;
   an object collection assembly structured and operable to receive and retain a plurality of object collection receptacles, each collection receptacle positioned adjacent a respective one of the diverting tubes such that each group of objects can be deposited into a respective corresponding one of the object collection receptacles, each collection receptacle comprising an information device attached thereto, each information device including information that stipulates the number of objects to be parsed and directed into the respective diverting tubes by the diverter assembly, and deposited into the respective collection receptacle, and
   a control system structured and operable to:
     read the information included in the information device of each collection receptacle that stipulates the number of objects to be deposited in the respective collection receptacle, and
     based on the stipulated number of objects to be deposited in the respective collection receptacle, control and coordinate operation of the singulating and counting assembly, the diverter assembly, and the object collection assembly to deposit the number of objects stipulated by the respective information device into each respective collection receptacle.

* * * * *